(12) United States Patent
Tamada et al.

(10) Patent No.: US 7,150,975 B2
(45) Date of Patent: Dec. 19, 2006

(54) HYDROGEL COMPOSITION FOR MEASURING GLUCOSE FLUX

(75) Inventors: Janet A. Tamada, Stanford, CA (US); Michael J. Tierney, San Jose, CA (US); Stephen C. Williams, El Granada, CA (US)

(73) Assignee: Animas Technologies, LLC, West Chester, PA (US)

( * ) Notice: Subject to any disclaimer, the term of this patent is extended or adjusted under 35 U.S.C. 154(b) by 387 days.

(21) Appl. No.: 10/643,631

(22) Filed: Aug. 18, 2003

(65) Prior Publication Data
US 2004/0087671 A1 May 6, 2004

Related U.S. Application Data

(60) Provisional application No. 60/404,807, filed on Aug. 19, 2002.

(51) Int. Cl.
*C12Q 1/54* (2006.01)

(52) U.S. Cl. .......................... 435/14; 604/20; 600/345; 600/347; 600/365

(58) Field of Classification Search .................. 435/14; 604/20; 600/345, 347, 365; 607/153
See application file for complete search history.

(56) References Cited

U.S. PATENT DOCUMENTS

| | | | |
|---|---|---|---|
| 4,020,830 A | 5/1977 | Johnson et al. |
| 4,200,098 A | 4/1980 | Ayer et al. |
| 4,406,827 A | 9/1983 | Carim |
| 4,474,570 A | 10/1984 | Ariura et al. |
| 4,492,622 A | 1/1985 | Kuypers |
| 4,684,558 A | 8/1987 | Keusch et al. |
| 4,702,732 A | 10/1987 | Powers et al. |
| 4,706,680 A | 11/1987 | Keusch et al. |
| 4,722,726 A | 2/1988 | Sanderson et al. |
| 4,722,761 A | 2/1988 | Cartmell et al. |
| 4,731,049 A | 3/1988 | Parsi |
| 4,764,164 A | 8/1988 | Sasaki |
| 4,777,954 A | 10/1988 | Keusch et al. |
| 4,968,297 A | 11/1990 | Jacobsen et al. |
| 4,989,607 A | 2/1991 | Keusch et al. |
| 5,036,861 A | 8/1991 | Sembrowich et al. |
| 5,037,380 A | 8/1991 | Jacobsen et al. |
| 5,057,072 A | 10/1991 | Phipps |
| 5,069,908 A | 12/1991 | Henley |
| 5,076,273 A | 12/1991 | Schoendorfer et al. |
| 5,134,057 A | 7/1992 | Kuypers et al. |
| 5,140,985 A | 8/1992 | Schroeder et al. |
| 5,143,071 A | 9/1992 | Keusch et al. |
| 5,152,758 A | 10/1992 | Kaetsu et al. |
| 5,205,297 A | 4/1993 | Montecalvo et al. |
| 5,279,543 A | 1/1994 | Glikfeld et al. |
| 5,291,887 A | 3/1994 | Stanley et al. |
| 5,330,527 A | 7/1994 | Montecalvo et al. |
| 5,340,722 A | 8/1994 | Wolfbeis et al. |
| 5,354,790 A | 10/1994 | Keusch et al. |
| 5,362,307 A | 11/1994 | Guy et al. |
| 5,362,308 A | 11/1994 | Chen et al. |
| 5,405,366 A | 4/1995 | Fox et al. |
| 5,428,123 A | 6/1995 | Ward et al. |
| 5,428,217 A | 6/1995 | Nakajima et al. |
| 5,442,858 A | 8/1995 | Wolters et al. |
| 5,636,632 A | 6/1997 | Bommannan et al. |
| 5,651,869 A | 7/1997 | Yoshioka et al. |
| 5,730,714 A | 3/1998 | Guy et al. |
| 5,735,273 A | 4/1998 | Kurnik et al. |
| 5,771,890 A | 6/1998 | Tamada |
| 5,786,216 A | 7/1998 | Dionne et al. |
| 5,823,957 A | 10/1998 | Faupel et al. |
| 5,827,183 A | 10/1998 | Kurnik et al. |
| 5,954,685 A | 9/1999 | Tierney |
| 5,965,380 A | 10/1999 | Heller et al. |
| 5,965,879 A | 10/1999 | Leviton |
| 5,989,409 A | 11/1999 | Kurnik et al. |
| 6,023,629 A | 2/2000 | Tamada |
| 6,083,710 A | 7/2000 | Heller et al. |
| 6,121,009 A | 9/2000 | Heller et al. |
| 6,139,718 A | 10/2000 | Kurnik et al. |
| 6,162,611 A | 12/2000 | Heller et al. |
| 6,299,578 B1 | 10/2001 | Kurnik et al. |
| 6,393,318 B1 | 5/2002 | Conn et al. |
| 6,515,078 B1 * | 2/2003 | Righettini .................. 525/302 |
| 6,587,705 B1 * | 7/2003 | Kim et al. .................. 600/347 |
| 6,615,078 B1 | 9/2003 | Burson et al. |
| 6,816,742 B1 * | 11/2004 | Kim et al. .................. 600/345 |
| 6,902,905 B1 * | 6/2005 | Burson et al. ................ 435/14 |

(Continued)

FOREIGN PATENT DOCUMENTS

EP 0 304 304 2/1989

(Continued)

OTHER PUBLICATIONS

Ackerman, N. Glucose Monitoring via Reverse Iontophoresis. ACS Symposium Series 2000 752(Controlled Drug Delivery)273-282.*

(Continued)

*Primary Examiner*—Ralph Gitomer
(74) *Attorney, Agent, or Firm*—RatnerPrestia

(57) ABSTRACT

The present invention relates to compositions for use in analyte monitoring devices. These compositions are useful to increase the flux of analyte across skin, tissue or mucosal surfaces. The compositions include hydrogels and collection reservoir systems comprising ionically conductive materials. The present invention also includes methods of making/manufacturing hydrogels or collection reservoir systems, collection assemblies comprising the hydrogels, electrode assemblies in combination with the hydrogels or collection reservoir systems, and methods of using the same.

21 Claims, 2 Drawing Sheets

U.S. PATENT DOCUMENTS

| | | | |
|---|---|---|---|
| 2003/0199745 A1* | 10/2003 | Burson et al. | 600/347 |
| 2004/0062759 A1* | 4/2004 | Abraham et al. | 424/94.1 |
| 2005/0170448 A1* | 8/2005 | Burson et al. | 435/14 |

FOREIGN PATENT DOCUMENTS

| | | |
|---|---|---|
| EP | 0 539 625 | 5/1993 |
| EP | 0 942 278 | 9/1999 |
| WO | WO 91/12772 | 9/1991 |
| WO | WO 92/07619 | 5/1992 |
| WO | WO 92/10234 | 6/1992 |
| WO | WO 93/10163 | 5/1993 |
| WO | WO 95/02357 | 1/1995 |
| WO | WO 96/00109 | 1/1996 |
| WO | WO 96/00110 | 1/1996 |
| WO | WO 97/02811 | 1/1997 |
| WO | WO 97/02811 A1 * | 1/1997 |
| WO | WO 97/10499 | 3/1997 |
| WO | WO 97/24059 | 7/1997 |
| WO | WO 97/38126 | 10/1997 |
| WO | WO 97/42882 | 11/1997 |
| WO | WO 97/42885 | 11/1997 |
| WO | WO 97/42886 | 11/1997 |
| WO | WO 97/42888 | 11/1997 |
| WO | WO 97/43962 | 11/1997 |
| WO | WO 99/58190 | 11/1999 |

OTHER PUBLICATIONS

Abstract of JP 56137899, Published Oct. 28, 1981.

Albin et al., "Theoretical and Experimental Studies of Glucose Sensitive Membranes," *Journal of Controlled Release* 6:267-291 (1987).

Allcock et al., "Activity of Urea Amidohydrolase Immobilized Within Poly[di(methoxyethoxyethoxy)phosphazene] Hydrogels," *Biomaterials* 15(7):502-506 (1994).

Asakura et al., "Immobilization of Glucose Oxidase on Nonwoven Fabrics with Bombyx mori Silk Fibroin Gel," *Journal of Applied Chemistry* 46(1):49-53 (1992).

D'Urso et al., "Poly(ethylene glycol)-Serum Albumin Hydrogel as Matrix for Enzyme Immobilization: Biomedical Applications," *Art. Cells. Blood Subs., and Immob. Biotech.* 23(5):587-595 (1995).

Glikfeld et al., "Noninvasive Sampling of Biological Fluids by Iontophoresis," *Pharm. Res. (US)* 6(11):988-990 (1989).

Heller et al., "Controlled Drug Release by Polymer Dissolution II: Enzyme-mediated Delivery Device," *J. Pharmaceut. Sci.* 68(7):919-921 (1979).

Kalisz, H. M., et al., "Purification of the Glycoprotein Glucose Oxidase From *Penicillium amagasakiense* by High-Performance Liquid Chromatography," *Journal of Chromatography* 521:245-250 (1990).

Kost et al., "Glucose Sensitibe Membranes Containing Glucose Oxidase: Activity, Swelling, and Permeability Studies," *J. Biomed. Materials Res.* 19(9):1117-1133(1985).

Lesho, et al, "A Photopatterned Glucose Responsive Hydrogel For Use in a Conductimetric Sensor", Materials Research Society Symposium Proceedings, 1994, vol. 331, pp. 193-198.

Meyerhoff et al., "On Line Continuous Monitoring of Subcutaneous Tissue Glucose in Men by Combining Portable Glucosensor with Microdialysis," *Diabetologia (Germany)* 35(11):1087-1092 (1992).

Newman,J.D., et al., "Catalytic Materials, Membranes, and Fabrication Technologies Suitable for the Construction of Amperometric Biosensors," *Analytical Chemistry* 67:4594-4599 (1995).

Tamada et al., "Noninvasive Glucose Monitoring," *JAMA* 282(19):1839-1844 (1999).

Updike et al., "The Enzyme Electrode," *Nature* 214:956-958 (1967).

Wang, Joseph,"Permselective Coatings for Amperometric Biosensing," Chapter 10 in ACS Symposium Series No. 487 *American Chemical Society* (1992).

Welfle, Dr. K., et al., "Glucose Oxidase of *Penicillium notatum*. Purification, Stability and Hydrodynamic Properties, " *Studia Biophysica* 138(3):245-260 (1990).

* cited by examiner

HYDROGEL COMPOSITION FOR MEASURING GLUCOSE FLUX

CROSS-REFERENCE TO RELATED APPLICATIONS

This application claims the benefit of U.S. Provisional Application Ser. No. 60/404,807, filed 19 Aug. 2002, which application is herein incorporated by reference in its entirety.

TECHNICAL FIELD

The present invention relates generally to compositions and methods for the enhancement of transdermal analyte flux.

BACKGROUND OF THE INVENTION

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by people with diabetes.

Diabetes is a major health concern, and treatment of the more severe form of the condition, Type 1 (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose to avoid or at least minimize the complications of Type 1 diabetes is well established. Patients with Type 2 (non-insulin-dependent) diabetes can also benefit from blood glucose monitoring in the control of their condition by way of diet and exercise.

Conventional blood glucose monitoring methods generally require the drawing of a blood sample (e.g., by finger-prick) for each test, and a determination of the glucose level using an instrument that reads glucose concentrations by electrochemical or colorimetric methods. Type 1 diabetics must obtain several fingerprick blood glucose measurements each day in order to maintain tight glycemic control. However, the pain and inconvenience associated with this blood sampling, along with the fear of hypoglycemia, has led to poor patient compliance, despite strong evidence that tight control dramatically reduces long-term diabetic complications. In fact, these considerations can often lead to an abatement of the monitoring process by the diabetic. See, e.g., The Diabetes Control and Complications Trial Research Group (1993) New Engl. J. Med. 329:977–1036.

Recently, various methods for determining the concentration of blood analytes without drawing blood have been developed. Some of these methods use hydrogels. A number of hydrophilic, polymeric compounds are known to form a gel in the presence of water, for example, 2% gelatin in water, obtained by the hydrolysis of collagen by boiling skin, ligaments, tendons, etc., will form a gel. A hydrogel may be formed by adding a solute, such as gelatin, to water at an elevated temperature to dissolve gelatin. The solution is then cooled and the solute(s) (e.g., solid gelatin components) forms submicroscopic crystalline particle groups which retain a great deal of solvent (generally water) in the interstices.

Gels may be formed from naturally occurring or synthetic materials and have a wide range of uses including photographic film, sizing, textile and paper adhesives, capsules and patches for medicinals, and patches used with electronic medical monitoring equipment. U.S. Pat. No. 5,405,366 to Fox et al. describes the formation of a non-stringy adhesive hydrophilic gel for use in delivering medicaments to a patent. The gels are formed, for example, by crosslinking the water soluble N-vinyl-2-pyrrolidone polymer under conditions such that the gel is free of unbound water. U.S. Pat. No. 5,143,071 to Keusch et al. also describes the formation of non-stringy adhesive gels by crosslinking poly(vinyl pyrrolidone) or poly(ethylene oxide).

Gel formulations for use in analyte monitoring devices have been described in PCT International Publication Nos. WO 97/02811 and WO 00/64533.

The present invention provides gel compositions, as well as compositions of ionically conductive materials, and methods that provide enhanced transdermal flux of analyte and improved performance of analyte monitoring systems.

SUMMARY OF THE INVENTION

The present invention relates to buffer compositions, ionically conductive materials, hydrogels, collection reservoir assemblies, collection assemblies, electrode assemblies comprising hydrogels, and collection assemblies/electrode assemblies (e.g., AutoSensors) for use in an analyte monitoring device. The present invention also includes methods of use and methods of making/manufacturing the compositions and assemblies of the present invention.

In one aspect, the present invention relates to a hydrogel composition for use in transdermal extraction of an analyte. The hydrogel composition may, for example, comprises a hydrophilic compound capable of forming a gel in the presence of water, an electrolyte, a phosphate buffer present at a concentration of between about 125 mM and about 500 mM, and a pH of between about pH 6.5 to about pH 8.5. Typically, the hydrophilic compound is a polymer and the polymer is present at a weight percent of between about 0.5% to about 40%, preferably about 1% to about 35%, more preferably about 2% to about 20% of the total weight of the hydrogel. The hydrophilic compound may, for example, be polyethylene oxide, polyvinyl alcohol, polyacrylic acid, polyvinyl pyrrolidone, and/or co-polymers thereof. In a preferred embodiment the hydrophilic compound comprises polyethylene oxide (e.g., at about 8% to about 12% of the total weight of the hydrogel for PEO Mr 600,000). In one embodiment the hydrophilic compound consists essentially of polyethylene oxide (e.g., between about 9% to about 11% of the total weight of the hydrogel for PEO Mr 600,000).

In one embodiment, the pH of the hydrogels of the present invention is between about pH 7 to about pH 8. The hydrogels may further comprise a cross-linking agent (present, for example, at a weight percent of from about 0.001% to about 2%). One exemplary cross-linking agent is bisacrylamide. The hydrogels of the present invention may also be irradiated, for example, using e-beam radiation, to promote cross-linking within the hydrogel. The phosphate buffer present in the hydrogels may comprise monobasic and dibasic phosphate. The monobasic and dibasic phosphate typically comprise phosphate and counter ions. The counter ions are, for example, sodium counter ions, potassium counter ions, or a mixture thereof. In some embodiments of the present invention the monobasic and dibasic phosphate the counter ion is potassium. The hydrogels of the present invention also comprise an electrolyte that may, for example, be a chloride salt. Such a chloride salt may, for example, be present at a weight percent of between about 0.25% to about 2%. In a preferred embodiment a chloride salt is present at a weight percent of 0.9%. Exemplary chloride salts include, but are not limited to, sodium chloride, potassium chloride, or a mixture thereof. Further, the hydrogels of the present invention may comprise an enzyme useful for detection of a selected analyte, for example, when the analyte is glucose the hydrogel may comprise glucose oxidase.

When the hydrogels of the present invention are employed in iontophoretic extraction of glucose across a skin or mucosal surface, glucose flux into the hydrogel is typically at least about 0.65 $nmol/cm^2hr$ at 0.25–0.32 $mA/cm^2$ current density. The glucose flux into the hydrogel may be, for example, at least about 0.8 $nmol/cm^2hr$, at least about 1.0 $nmol/cm^2hr$, or at least about 1.1 $nmol/cm^2hr$.

Typically the hydrogels of the present invention have a background signal of less than about 100 nA when acting as an electrolyte for an amperometric sensing electrode.

The hydrogels of the present invention may further comprise one or more biocides. Exemplary biocides include, but are not limited to, chlorinated hydrocarbons, organometallics, metallic salts, organic sulfur compounds, phenolic compounds, quaternary ammonium compounds, surfactants, membrane-disrupting agents, and combinations thereof. In one embodiment of the present invention, the biocide is undecylenic acid and/or a salt thereof.

In another aspect the present invention relates to electrode assemblies comprising, a first hydrogel having first and second surfaces, the hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5, and a first iontophoretic electrode, wherein the first iontophoretic electrode is aligned to contact the second surface of the first hydrogel. Electrode assemblies may further comprise a first sensing electrode, wherein the first sensing electrode is aligned to contact the second surface of the first hydrogel. In some embodiments, the sensing electrode comprises a reactive surface comprising a platinum group metal and a polymer binder. Electrode assemblies may further comprise a second hydrogel having first and second surfaces, and a second iontophoretic electrode, wherein the second iontophoretic electrode is aligned to contact the second surface of the second hydrogel. Further, the electrode assembly may comprise a second sensing electrode, wherein the second sensing electrode is aligned to contact the second surface of the second hydrogel.

In yet another aspect the present invention relates to electrode assemblies comprising a first hydrogel having first and second surfaces, the hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5, and a first sensing electrode, wherein the first sensing electrode (i) is aligned to contact the second surface of the first hydrogel, and (ii) has a reactive surface comprising a platinum group metal and a polymer binder. Electrode assemblies may further comprise a first iontophoretic electrode, wherein the first iontophoretic electrode is aligned to contact the second surface of the first hydrogel. Further, the electrode assemblies may include a second hydrogel having first and second surfaces, and a second sensing electrode, wherein the second sensing electrode (i) is aligned to contact the second surface of the first hydrogel, and (ii) has a reactive surface comprising a platinum group metal and a polymer binder, as well as a second iontophoretic electrode, wherein the second iontophoretic electrode is aligned to contact the second surface of the second hydrogel.

In another aspect, the present invention includes methods of making/manufacturing a collection assembly, for use in an iontophoretic sampling device useful to monitor a selected analyte or derivatives thereof present in a biological system. In one method, first and second collection inserts are provided wherein each insert comprising a hydrogel having first and second surfaces, each hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5. A mask is provided wherein the mask comprises (i) a material that is substantially impermeable to the selected analyte or derivatives thereof, and (ii) inner and outer faces, wherein the mask defines first and second openings and a border. Further, a retaining layer is provided wherein the retaining layer comprises inner and outer faces, and the retaining layer defines first and second openings and a border. In the method, the inner face of the mask is positioned in facing relation with the first surface of each collection insert, such that (i) the first and second openings of the mask are, respectively, aligned with the first and second collection inserts (ii) each opening of the mask exposes at least a portion of the first surface of the collection insert with which it is aligned, and (iii) the border extends beyond the first surface of each of the collection inserts to provide an overhang. The inner face of the retaining layer is positioned in facing relation with the second surface of each collection insert, such that (i) the first and second openings of the retaining layer are, respectively, aligned with the first and second collection inserts, (ii) each opening of the retaining layer exposes at least a portion of the second surface of the collection insert with which it is aligned, and (iii) the border extends beyond the first surface of each of the collection inserts to provide an overhang. This method results in production of a collection assembly. In some embodiments the collection assembly is used to monitor glucose present in the biological system. In this case the hydrogels typically comprise glucose oxidase.

In yet another aspect the present invention relates to a method of making/manufacturing a collection assembly/ electrode assembly (e.g., an AutoSensor assembly) for use in an iontophoretic sampling device useful to monitor a selected analyte or derivatives thereof present in a biological system. In the method, first and second collection inserts are provided where each insert comprising a hydrogel having first and second surfaces, each hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5. A mask is provided that is (i) a substantially planar material that is substantially impermeable to the selected analyte or derivatives thereof, and (ii) inner and outer faces, wherein the mask defines first and second openings and a border. A retaining layer is also provided, where the retaining layer comprises inner and outer faces. The retaining layer also defines first and second openings and a border. First and second electrode assemblies are also provided, each electrode assembly comprising (i) first and second surfaces, and (ii) the first surface comprising an electrode. A support tray is also provided. The inner face of the mask is positioned in facing relation with the first surface of each collection insert, such that (i) the first and second openings of the mask are, respectively, aligned with the first and second collection inserts, (ii) each opening of the mask exposes at least a portion of the first surface of the collection insert with which it is aligned, and (iii) the border extends beyond the first surface of each of the collection inserts to provide an overhang. The inner face of the retaining layer is positioned in facing relation with the second surface of each collection insert, such that (i) the first and second openings of the retaining layer are, respectively, aligned with the first and second collection inserts, (ii) each opening of the retaining layer exposes at least a portion of the second surface of the collection insert with which it is aligned, and (iii) the border extends beyond the first surface of each of the collection inserts to provide an overhang. The first and second electrode assemblies are positioned relative to the outer face of the retaining layer such that a first surface of the electrode of the first electrode assembly is aligned with the first opening in the retaining layer, and a first surface of the electrode of the second electrode assembly is aligned with the second opening in the retaining layer. The support tray is positioned such that it contacts the second surface of each electrode assembly. This method results in production of a collection assembly/electrode assembly. In some embodiments the collection assembly/electrode assembly is used to monitor glucose present in the biological system. In this case the hydrogels typically comprise glucose oxidase.

In yet another aspect, the present invention relates to collection reservoir systems for transdermal extraction of an analyte. A collection reservoir system typically comprises one or more collection reservoirs, wherein at least one collection reservoir comprises an ionically conductive material comprising, for example, electrolyte, phosphate buffer present at a concentration of between about 125 mM and about 500 mM, and a pH of between about pH 6.5 to about pH 8.5, preferably the pH is between about pH 7 to about pH 8. The ionically conductive material may further comprise a hydrophilic polymer. The phosphate buffer typically is made up of monobasic and dibasic phosphate. The monobasic and dibasic phosphate comprise phosphate and counter ions. The counter ions are sodium counter ions, potassium counter ions, or a mixture thereof. In some embodiments the monobasic and dibasic phosphate counter ion is potassium. The electrolyte may, for example, be a chloride salt. The chloride salt may be present at a weight percent of between about 0.25% to about 2%, preferably at a weight percent of about 0.9%. The chloride salt may be sodium chloride, potassium chloride, or a mixture thereof. The collection reservoir, comprising ionically conductive material, may further comprise an enzyme useful for detection of the analyte, for example, when the analyte is glucose the collection reservoir may comprise glucose oxidase.

When the collection reservoir systems, comprising ionically conductive material, of the present invention are employed in iontophoretic extraction of glucose across a skin or mucosal surface, glucose flux into the collection reservoir is typically at least about 0.65 nmol/cm$^2$hr at 0.25–0.32 mA/cm$^2$ current density. The glucose flux into the collection reservoir may be, for example, at least about 0.8 nmol/cm$^2$hr, at least about 1.0 nmol/cm$^2$hr, or at least about 1.1 nmol/cm$^2$hr.

In a further aspect, the present invention includes methods of making/manufacturing collection reservoir systems of the present invention for use in an iontophoretic sampling device useful to monitor a selected analyte or derivatives thereof present in a biological system. In one method, one or more collection reservoirs is provided and to at least one collection reservoir is added an appropriate volume of an ionically conductive material, comprising electrolyte, and phosphate buffer present at a concentration of between about 125 mM and about 500 mM, with a pH of between about pH 6.5 to about pH 8.5.

In yet another aspect of the invention, a method of increasing transdermal flux of an analyte is described. In the method, the analyte is extracted across a tissue surface using an iontophoretic sampling device, wherein the sampling device comprises a hydrogel composition or collection reservoir system comprising ionically conductive material as described herein. The increase in transdermal flux is evaluated relative to extracting the analyte using the iontophoretic sampling device wherein the hydrogel composition instead comprises a hydrophilic compound capable of forming a gel in the presence of water, an electrolyte, a phosphate buffer present at a concentration of equal to or less than 100 mM, and a pH of about pH 7 to about pH 8. In one embodiment the tissue surface is the stratum corneum of skin tissue. In another embodiment the tissue surface is a mucosal surface.

Yet another aspect of the invention includes methods of determining the concentration of an analyte in a mammalian subject using a monitoring system comprising an iontophoretic sampling device. In one method, a first surface of a hydrogel or collection reservoir system described herein is in contact with a tissue surface of the mammalian subject, wherein (i) a second surface of the hydrogel is in contact with a first iontophoretic electrode and a first sensing electrode, and (ii) the monitoring system comprises an electrode assembly, the electrode assembly comprising the first iontophoretic electrode, the first sensing electrode, and a second iontophoretic electrode. A current is provided to the first and second iontophoretic electrodes in an amount sufficient to effect the extraction of the analyte through the mammalian subject's skin, into the hydrogel and to the catalytic surface of the first sensing electrode. A potential is provided to the first sensing electrode in an amount sufficient to drive electrochemical detection of the analyte or an analyte-related chemical signal. Electrical current, generated by the electrochemical detection at the electrode, is measured. The measured current is then correlated to a concentration or amount of analyte in the mammalian subject.

The tissue surface may, for example, be the stratum corneum of skin tissue or a mucosal surface. When the analyte is glucose, the hydrogel or collection reservoir system typically comprises glucose oxidase and the analyte related chemical signal is hydrogen peroxide.

These and other embodiments of the present invention will readily occur to those of ordinary skill in the art in view of the disclosure herein.

DETAILED DESCRIPTION OF THE INVENTION

Figure 1A:
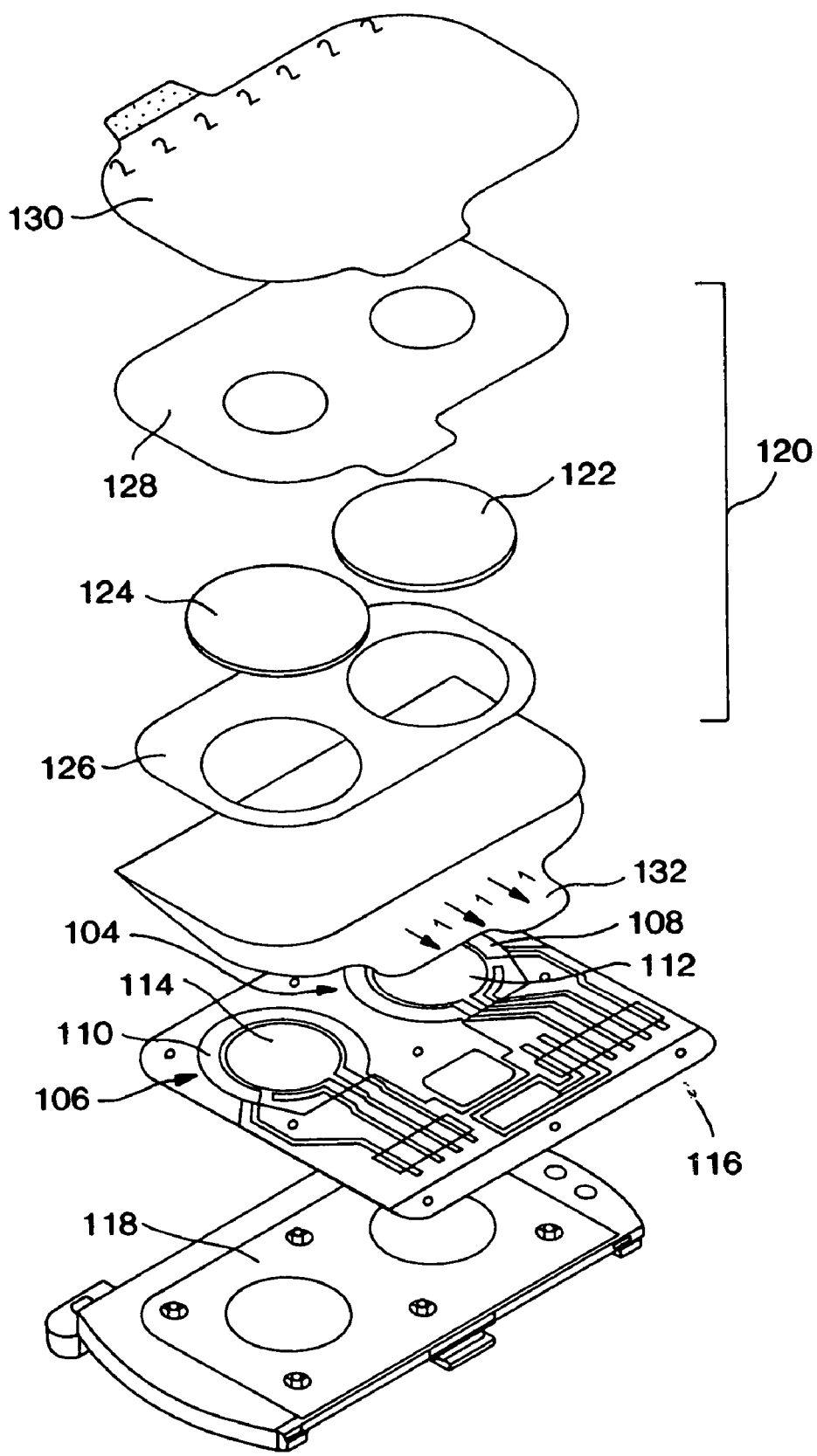
FIG. 1A presents a schematic of an exploded view of exemplary components comprising one embodiment of a GlucoWatch® (Cygnus, Inc., Redwood City, Calif.) AutoSensor for use in a monitoring system. This AutoSensor exemplifies one embodiment of a collection assembly/electrode assembly.

All patents, publications, and patent applications cited in this specification are herein incorporated by reference as if each individual patent, publication, or patent application was specifically and individually indicated to be incorporated by reference in its entirety for all purposes.

1.0.0 DEFINITIONS

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a reservoir" includes a combination of two or more such reservoirs, reference to "an analyte" includes one or more analytes, mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Santa Clara, Calif.; and, National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., PCT International Publication No. WO 91/12772; U.S. Pat. No. 5,636,632), suction, electroporation, thermal poration, passive diffusion (see, e.g., PCT International Publication Nos.: WO 97/38126; WO 97/42888, WO 97/42886, WO 97/42885, and WO 97/42882; and WO 97/43962), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88–93; PCT International Publication Nos. WO 99/44507, WO 99/44638, and WO 99/40848). Iontophoretic sampling devices are described, for example, in PCT International Publication No. WO 97/24059; European Patent Application EP 0942 278; PCT International Publication Nos. WO 96/00110, WO 97/10499; U.S. Pat. Nos. 5,279,543; 5,362,307; 5,730,714; 5,771,890; 5,989,409; 5,735,273; 5,827,183; 5,954,685, 6,023,629, and 6,298,254. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system," "analyte monitoring system," or "analyte monitoring device" refers to a system useful for obtaining frequent measurements of a physiological analyte present in a biological system (e.g., analyte amount or concentration in blood or interstitial fluid). Such a system may comprise, but is not limited to, a sensing device and one or more microprocessors in operative combination with the sensing device, or a sampling device, a sensing device, and one or more microprocessors in operative combination with the sampling device and the sensing device.

A "measurement cycle" typically comprises sensing of an analyte in a sample, for example, using a sensing device, to provide a measured signal, for example, a measured signal response curve. Typically a series of measurement cycles provides a series of measured signals. The measurement cycle may further comprise, for example, extraction of an analyte from a subject, using, for example, a sampling device. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g., second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, for example, stratum corneum, or mucosal tissue. Aspects of the invention, which are described herein in the context of "transdermal," unless otherwise specified, are meant to apply to both transdermal and transmucosal techniques.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890, 6,023,629, 6,298,254, and PCT International Publication No. WO 96/00109.

The term "reverse iontophoresis" refers to the movement of a substance from a biological fluid across a membrane by way of an applied electric potential or current. In reverse iontophoresis, a reservoir is provided at the tissue surface to receive the extracted material, as used in the GlucoWatch® (Cygnus, Inc., Redwood City, Calif.) biographer and GlucoWatch® G2™ (Cygnus, Inc., Redwood City, Calif.) biographer glucose monitors (see, e.g., Tamada et al. (1999) JAMA 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device" or "sensing mechanism" encompasses any device that can be used to measure the concentration or amount of an analyte, or derivative thereof, of interest. Preferred sensing devices for detecting analytes (e.g., in blood or interstitial fluid) generally include electrochemical devices, optical and chemical devices and combinations thereof. Examples of electrochemical devices include the Clark electrode system (see, e.g., Updike, et al., (1967) Nature 214:986–988), and other amperometric, coulometric, or potentiometric electrochemical devices, as well as, optical methods, for example UV detection or infrared detection (e.g., U.S. Pat. No. 5,747,806). For example, U.S. Pat. No. 5,267,152 to Yang et al. describes a noninvasive technique of measuring blood glucose concentration using near-IR radiation diffuse-reflection laser spectroscopy. Near-IR spectrometric devices are also described in U.S. Pat. No. 5,086,229 to Rosenthal, et al., U.S. Pat. No. 5,747,806, to Khalil, et al., and U.S. Pat. No. 4,975,581, to Robinson, et al. Additional examples include sensing systems used for continuous monitoring of an analyte amount or concentration in a subject, for example, as described in U.S. Pat. Nos. 6,134,461 and 6,175,752.

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface that converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some biosensor electrode embodiments are described in EP 0 942 278, GB 2 335 278, U.S. Pat. Nos. 6,042,751, 6,587,705, and PCT International Publication No. WO 03/054070. Some catalytic materials, membranes, and fabrication technologies suitable for the construction of amperometric biosensors are also described by Newman, J. D., et al. (1995) Analytical Chemistry 67:4594–4599.

The "sensor element" can include components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (2) converts a chemical signal (for example, hydrogen peroxide) into an electrical signal (e.g., an electrical current); and (3) defines the electrode surface area that, when composed of a reactive material, is sufficient to drive the electrochemical reaction at a rate sufficient to generate a detectable, reproducibly measurable, electrical signal when an appropriate electrical bias is supplied, that is correlatable with the amount of analyte present in the electrolyte. Further, the reactive surface or reactive face may be in contact with the surface of an ionically conductive material that contains an analyte or through which an analyte, or a derivative thereof, flows from a source.

"Ionically conductive material" compositions are described herein. An ionically conductive material provides a composition that is electrically conductive and through which electrochemically active species can diffuse. The ionically conductive material is typically in the form of a hydrogel. The ionically conductive material may be, for example, a solid, liquid, or semi-solid material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. The ionically conductive material is typically in the form of a hydrogel. The ionically conductive material may comprise a biocide. For example, during manufacture of a collection assembly, one or more biocides may be incorporated into the ionically conductive material. Biocides of interest include, but are not limited to, compounds such as chlorinated hydrocarbons; organometallics; metallic salts; organic sulfur compounds; phenolic compounds (including, but not limited to, a variety of Nipa Hardwicke Inc. (Wilmington, Del.) liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

"Hydrophilic compound" refers to a monomer that attracts, dissolves in, or absorbs water. The hydrophilic compounds for use according to the invention include, but are not limited to, one or more of the following: carboxy vinyl monomer, a vinyl ester monomer, an ester of a carboxy vinyl monomer, a vinyl amide monomer, a hydroxy vinyl monomer, a cationic vinyl monomer containing an amine or a quaternary ammonium group. The monomers can be used to make the polymers or co-polymers including, but not limited to, polyethylene oxide (PEO), polyvinyl alcohol, polyacrylic acid, and polyvinyl pyrrolidone (PVP).

The term "buffer" refers to one or more components that are added to a composition in order to adjust or maintain the pH of the composition.

The term "electrolyte" refers to a component of the ionically conductive medium that allows an electrical current to flow within the medium. This component of the ionically conductive medium can be one or more salts or buffer components, but is not limited to these materials. For example, chloride salts (e.g., sodium chloride (NaCl) and potassium chloride (KCl)) are salts that may be employed singly or together as electrolyte.

The term "collection reservoir" is used to describe any suitable containment method or device for containing a sample extracted from a biological system. For example, the collection reservoir can be a receptacle comprising a material that is ionically conductive (e.g., water with ions therein), or alternatively it can be a material, such as a sponge-like material or hydrophilic polymer, used to keep the ionically conductive material in place. Such collection reservoirs can be in the form of a sponge, porous material, or hydrogel (for example, in the shape of a disk or pad). Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising one or more collection reservoir (or collection insert) located, for example, between a mask layer and a retaining layer. Hydrogels are exemplary "collection inserts."

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel or collection reservoir. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,827,183, 5,735,273, 6,141,573, 6,201,979, 6,370,410, and 6,529,755.

The term "gel retaining layer" or "gel retainer" refers to a component of a collection assembly that is substantially planar and typically contacts both the collection insert layer and the electrode assembly. See, for example, U.S. Pat. Nos. 6,393,318, 6,341,232, and 6,438,414.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a collection assembly (e.g., a mask layer, collection insert layer, a gel retaining layer), an electrode assembly, and typically a support tray. The AutoSensor assembly may also include liners where the layers are held in approximate, functional relationship to each other. Exemplary collection assemblies and AutoSensor structures are described, for example, U.S. Pat. Nos. 5,827,183, 5,735,273, 6,141,573, 6,201,979, 6,370,410, 6,393,318, 6,341,232, 6,438,414, and 6,529,755. One such AutoSensor assembly is manufactured by Cygnus, Inc., Redwood City, Calif. These exemplary collection assemblies and AutoSensors may be modified by use of the ionically conductive materials (e.g., hydrogels) of the present invention. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of a conductive polymer composite film (e.g., an electrode ink formulation) onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Decay" refers to a gradual reduction in the magnitude of a quantity, for example, a current detected using a sensor electrode where the current is correlated to the concentration of a particular analyte and where the detected current gradually reduces but the concentration of the analyte does not.

"Skip" or "skipped" signals refer to data that do not conform to predetermined criteria (for example, error-associated criteria as described in U.S. Pat. No. 6,233,471). A skipped reading, signal, or measurement value typically has been rejected (i.e., a "skip error" generated) as not being reliable or valid because it does not conform with data integrity checks, for example, where a signal is subjected to a data screen which invalidates incorrect signals based on a detected parameter indicative of a poor or incorrect signal.

1.1.0 GlucoWatch Biographer Monitoring Devices

The terms "GlucoWatch biographer" and "GlucoWatch G2 biographer" refer to two exemplary devices in a line of GlucoWatch biographer monitoring devices developed and manufactured by Cygnus, Inc., Redwood City, Calif.

GlucoWatch biographers analyte monitoring devices provide automatic, frequent, and noninvasive glucose measurements. The first-generation device, the GlucoWatch® (Cygnus, Inc., Redwood City, Calif.) biographer, provides up to 3 readings per hour for as long as 12 hours after a 3-hour warm-up period and a single blood glucose (BG) measurement for calibration. The second-generation device, the GlucoWatch® G2™ (Cygnus Inc., Redwood City, Calif.) biographer, provides up to six readings per hour for as long as 13 hours after a single BG measurement for calibration. These devices utilize a reverse iontophoresis to extract glucose through the skin. The glucose is then detected by an amperometric biosensor. GlucoWatch biographer monitoring devices are small devices typically worn on the forearm that contain sampling and detection circuitry, and a digital display. Clinical trials on subjects with Type 1 and Type 2 diabetes have shown excellent correlation between Gluco-Watch biographer readings and serial finger-stick BG measurements (see, e.g., Garg, S. K., et al., Diabetes Care 22, 1708 (1999); Tamada, J. A., et al., JAMA 282, 1839 (1999)). However, the first-generation GlucoWatch biographer measurement period is limited to 12 hours, due to decay of the biosensor signal during use. The second-generation device extends the measurement period to up to 13 hours.

GlucoWatch biographer monitoring devices have several advantages. Clearly their non-invasive and non-obtrusive nature encourages more glucose testing among people with diabetes. Of greater clinical relevance is the frequent nature of the information provided. GlucoWatch biographer monitoring devices provide the more frequent monitoring desired by physicians in an automatic, non-invasive, and user-friendly manner. The automatic nature of the systems also allow monitoring to continue even while the patient is sleeping or otherwise unable to test. The GlucoWatch biographer and GlucoWatch G2 biographer are the only non-invasive, frequent and automatic glucose-monitoring devices approved by the U.S. Food and Drug Administration and commercially available.

1.1.1 Device Description of GlucoWatch Biographer Monitoring Devices

GlucoWatch biographer monitoring devices contain the electronic components that supply iontophoretic current and controls current output and operating time. They also control the biosensor electronics, as well as receive, process, display and store data. Data can also be uploaded from GlucoWatch biographer monitoring devices to a personal computer, a computer network, personal digital assistant device, etc. They have bands to help secure them to sites on the forearm.

The AutoSensor is a consumable part of the devices that provides up to 13 hours of continuous glucose measurement (in the second-generation device). The AutoSensor is discarded after each wear period. It fits into the back of a GlucoWatch biographer monitoring device and contains electrodes for delivery of iontophoretic current, sensor electrodes for sensing the glucose signal, and glucose-oxidase-containing hydrogel pads for glucose collection and conversion to hydrogen peroxide. There are two gel/electrode sets on each AutoSensor, denoted as A and B.

Iontophoresis utilizes the passage of a constant low-level electrical current between two electrodes applied onto the surface of the skin. This technique has been used, for example, to deliver transdermally ionic (charged) drugs (Sinh J., et al., Electrical properties of skin, in "Electronically controlled drug delivery," Berner B, and Dinh S M, eds., Boca Raton, La.: CRC Press (1998), pp. 47–62.). On the other hand, electrolyte ions in the body can also act as the charge carriers and can lead to extraction of substances from the body outward through the skin. This process is known as "reverse iontophoresis" or iontophoretic extraction (Rao, G. et al., Pharm. Res. 10, 1751 (2000)). Because skin has a net negative charge at physiological pH, positively charged sodium ions are the major current carriers across the skin. The migration of sodium ions toward the iontophoretic cathode creates an electro-osmotic flow, which carries neutral molecules by convection. However, only compounds with small molecular weight pass through the skin, so that, for example, no proteins are extracted. Moreover, major interfering species (e.g., ascorbate and urate) are collected at anode. As a result of these unique charge and size exclusion properties of reverse iontophoresis, glucose is preferentially extracted at the cathode, and the obtained sample is very clean. This is in contrast to implantable glucose monitoring devices (Gross, T. M., Diabetes Technology and Therapeutics 2, 49 (2000); Meyerhoff, C., et al., Diabetologia, 35, 1087 (1992); Bolinder, J., et al., Diabetes Care 20, 64 (1997)) for which ascorbate and urate (as well as some proteins) are known to produce an interfering signal.

The feasibility of iontophoretic glucose extraction for glucose monitoring was demonstrated in human subjects (Tamada, J. A., et al., Nat. Med. 1, 1198 (1995)). In feasibility studies with human subjects, glucose transport correlated well with BG in a linear manner. However, the sensitivity (i.e., the amount of glucose extracted) varied among individuals and skin sites (Tamada, J. A., et al., Nat. Med. 1, 1198 (1995)). A single-point calibration was found to compensate for this variability. Reverse iontophoresis yields micromolar concentrations of glucose in the receiver solution, which is about three orders of magnitude less than that found in blood.

To accurately measure this small amount of glucose, GlucoWatch biographer monitoring devices utilize an amperometric biosensor (Tierney, M. J., et al., Clin. Chem. 45, 1681 (1999)). The glucose oxidase (GOx) enzyme in hydrogel disks (where glucose is collected via reverse iontophoresis) catalyzes the reaction of glucose with oxygen to produce gluconic acid and hydrogen peroxide,

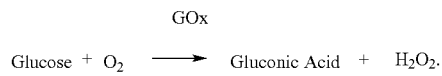

Glucose exists in two forms: α- and β-glucose, which differ only in the position of a hydroxyl group relative to the plane of the hexose. At equilibrium (also in blood and in interstitial fluid), the two forms are in proportion of about 37% α and about 63% β. As glucose enters the hydrogel, it diffuses throughout, and only the β-form of glucose reacts with the glucose oxidase enzyme. As β-form is depleted, the α-form then converts (mutarotates) to the β-form. The products of the glucose oxidase reaction (hydrogen peroxide and gluconic acid) also diffuse throughout the gel. Finally, hydrogen peroxide ($H_2O_2$) is detected at a platinum-containing working electrode in the sensor via the electro-catalytic oxidation reaction,

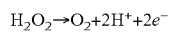

producing measurable electrical current, and regenerating $O_2$. Thus, ideally, for every glucose molecule extracted, two electrons are transferred to the measurement circuit. Integration over time of the resulting electric current leads to the total charge liberated at the electrode, and the latter is correlated to the amount of glucose collected through the skin.

The structure of the second-generation device is very similar to the first-generation device; there are no differences in the AutoSensor. Extraction and detection are achieved using two hydrogel pads (A and B) placed against the skin. The side of each pad away from the skin is in contact with an electrode assembly containing two sets of iontophoretic and sensing elements. The two electrode sets complete the iontophoretic circuit. During operation, one iontophoretic electrode is cathodic and the other anodic, enabling the passage of current through the skin. As a consequence, glucose and other substances are collected in the hydrogel pads during the iontophoretic extraction period. The iontophoretic time interval is adjusted to minimize skin irritation and power requirements, yet extract sufficient glucose for subsequent detection. It has been found that a useful time for extraction of glucose is about three minutes.

On the side of each hydrogel pad, away from the skin and adjacent to the annular iontophoretic electrode, are the sensing electrodes. There are two sensing electrodes, noted as sensor A and B. These circular sensing electrodes are composed of a platinum composite, and are activated by applying a potential of 0.3–0.8 V (relative to a Ag/AgCl reference electrode). At these applied potentials, a current is then generated from the reaction of $H_2O_2$ (generated from extracted glucose) that has diffused to the platinum sensor electrode.

1.1.2 Device Operation of GlucoWatch Biographer Monitoring Devices

Each 20 minute glucose measurement cycle consists of three minutes of extraction, and seven minutes of biosensor activation, followed by three minutes of extraction at the opposite iontophoresis current polarity, and seven additional minutes of biosensor activation.

In the first half-cycle, glucose is collected in the hydrogel at the iontophoretic cathode (Sensor B). As the glucose is collected, it reacts with the glucose oxidase in the hydrogel to produce hydrogen peroxide ($H_2O_2$). At the end of the three-minute collection period, the iontophoretic current is stopped, and the biosensors activated for seven minutes to measure the accumulated $H_2O_2$. This period is chosen so that the vast majority of the extracted glucose is converted to $H_2O_2$, and that the vast majority of this peroxide diffuses to the platinum electrode, and subsequently oxidizes to generate a current. Because the underlying physical and chemical processes (including, but not limited to, diffusion, glucose mutarotation, and electro-catalytic oxidation reaction at the sensing electrodes) are rather slow, not all of the extracted glucose and $H_2O_2$ is consumed during the seven-minute measurement cycle. However, the integrated current (or charge) signal over this seven-minute interval is sufficiently large and remains proportional to the total amount of glucose that entered the hydrogel pad during the iontophoresis interval. In the process of detection, majority of $H_2O_2$ is depleted. This cleans out the hydrogel to be ready for the next collection period. Moreover, before sensor B will be collecting and measuring glucose again, it has to act as an iontophoretic anode first. The extraction-sensing cycles have been designed so that there will be no peroxide left in the hydrogel after this period. During the initial three-minute period, there is also extraction at the anode (sensor A), primarily of anionic species such as urate and ascorbate. These electrochemically active species are also purged from the anodic reservoir during the seven-minute biosensor period.

In the second half-cycle of the measurement cycle, the iontophoretic polarity is reversed, so that glucose collection at the cathode occurs in the second reservoir (sensor A), and the anionic species are collected in the first reservoir (sensor B). The biosensor is again activated to measure glucose at the cathode (now sensor A) and to purge electrochemically active species for the anode (sensor B). The combined twenty-minute process is repeated to obtain each subsequent glucose reading.

The raw data for each half-cycle are collected for both A and B sensors as 13 discrete current values measured as functions of time over the seven minutes (providing a measured signal response curve). When the sensor circuits are activated in the cathodic cycle, $H_2O_2$ (converted from glucose) reacts with the platinum electrode to produce a current, which monotonically declines with time over the seven-minute detection cycle. A current signal of similar shape is also generated in the anodic cycle (curve with data points represented with diamonds). This signal is due, in large part, to ascorbic and uric acids. In both cases the current transients come down to a background of approximately 180 nA rather than zero. The background current, termed the baseline background, does not vary much over time, indicating that it is likely the result of the sum of a number of low concentration species. In order to extract the glucose-related signal only, the background is subtracted from the total current signal. Although the background, once subtracted, does not introduce a significant bias to the glucose measurement, it does significantly decrease the signal-to-noise ratio of the measurement in the hypoglycemic region. This increased noise increases the potential error in the glucose measurement in the hypoglycemic range. It is therefore important to determine the background current as accurately as possible. In some cases there is not enough time in the seven-minute cathodic cycle to consume $H_2O_2$ completely and the current at the end of this cycle is still decreasing. Therefore this measurement may not always provide the best estimation of the background. On the other hand, it was found that the current stabilizes earlier and more consistently in anodic cycles. Therefore, the baseline background is typically determined as the average of the last two current readings of the preceding anodic cycle.

After the background subtraction, the cathodic current signal is integrated to calculate the electrical charge (on the order of μC) liberated at the cathode, which is proportional to the total amount of glucose extracted through the skin. Integration has the added value that it compensates for variations in gel thickness and temperature, as these variables affect only the rate, not the extent of reaction. The integrated signal at the cathodal sensor for each half cycle are averaged as $(C_A+C_B)/2$, a procedure that improves signal-to-noise ratio of the system.

Finally, the averaged charge signal is converted into a glucose measurement based on a patient's finger-stick calibration value (entered at the beginning of the monitoring period). From the calibration, a relationship between charge signal detected by the sensor and blood glucose is determined. This relationship is then used to determine glucose values based on biosensor signal measurements. The latter is achieved by utilizing a signal processing algorithm called Mixtures of Experts (MOE) (Kurnik, R. T., Sensors and Actuators B 60, 1 (1999); U.S. Pat. Nos. 6,180,416, and 6,326,160). The MOE algorithm incorporates: integrated charge signal, calibration glucose value, charge signal at calibration, and time since calibration (i.e., elapsed time). It calculates each glucose reading as a weighted average of predictions obtained from three independent linear models (called Experts), which depend on the four inputs and a set of 30 optimized parameters. Equations to perform this data conversion have been developed, optimized, and validated on a large data set consisting of GlucoWatch biographer and reference BG readings from clinical trials on diabetic subjects. This data conversion algorithm is programmed into a dedicated microprocessor in the GlucoWatch biographer.

The GlucoWatch G2 biographer reduces warm-up time (from three to two hours), increases the number of readings per hour (up to six versus up to three), extends AutoSensor duration (use for 12 to 13 hours), and provides predictive low-alert alarms. The increase in the number of readings provided by the GlucoWatch G2 biographer is the result of a modified data processing algorithm that provides a series of moving average values based on the glucose-related signals from sensors A and B. The GlucoWatch G2 biographer uses the same AutoSensor as the first-generation GlucoWatch biographer.

The glucose readings provided by the GlucoWatch biographers lag the actual blood glucose by about 15–20 minutes. This lag is derived not only from the inherent measurement lag resulting from the time-averaging of glucose signals performed by the GlucoWatch biographers, but also from the physiological differences between the concentration of glucose in interstitial fluid (which is measured by the GlucoWatch biographers) and the instantaneous glucose concentration in blood (as typically measured via a finger prick). The measurement lag is 13.5 minutes. A GlucoWatch biographer glucose reading corresponds to the average glucose concentration in interstitial fluid during the two preceding 3-minute extraction periods (separated by the first 7-minute sensing period) and it is provided to the user after the second 7-minute sensing period, resulting in the 13.5 minute measurement lag. The additional physiological lag is estimated as about 5 minutes.

The GlucoWatch biographers perform a series of data integrity checks before computing each glucose value. The checks, called screens, selectively prevent certain glucose values from being reported to the user based on certain environmental, physiological, or technical conditions. The screens are based on four measurements taken during the course of wear: current (electrochemical signal), iontophoretic voltage, temperature, and skin surface conductance. Removed points are called skips. For example, if sweat is detected by an increased skin surface conductance, the glucose reading is skipped because the sweat could contain glucose, which could interfere with the glucose extracted from the skin during the iontophoretic period. Other skips are based on noise detected in the signal.

2.0.0 Modes of Carrying Out the Invention

Before describing the present invention in detail, it is to be understood that this invention is not limited to particular types of compositions, or methods of making or using the same, as use of such particulars may be selected in view of the teachings of the present specification. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1.0 General Overview of the Inventions

The present invention relates to the detection of analytes and/or derivatives thereof (e.g., biologically important molecules, such as glucose) that are collected across a membrane, a tissue surface (e.g., the stratum corneum), or mucosal membranes. The present invention provides compositions for transporting the analytes and/or derivatives thereof across such membranes. The present invention also includes the detection of such analytes (and/or derivatives thereof). In one aspect, the compositions of the present invention are employed in devices used to determine the in vivo amount or concentration of the analyte.

In one aspect, the present invention provides hydrogel compositions. Such hydrogel compositions may, for example, be used in transdermal extraction of an analyte. An exemplary hydrogel composition of the present invention comprises a hydrophilic compound capable of forming a gel in the presence of water, an electrolyte, a phosphate buffer present at a concentration of between about 125 mM and about 500 mM, and a pH of between about pH 6.5 to about pH 8.5. In a preferred embodiment of the present invention, the hydrogel composition does not include a humectant.

The hydrogels of the present invention can be used in devices that employ transdermal extraction for the detection and/or quantification of analyte in a subject. For example, the hydrogels of the present invention are typically placed in contact with an electrode. The electrode/hydrogel combination is placed on a membrane surface, for example, on the skin of a subject in whom the analyte of interest is being monitored. In one embodiment, a current is generated such that the current results in the transport of the analyte and/or derivative thereof across the membrane and into the hydrogel, wherein the amount of the analyte may be determined and the concentration in the subject calculated. In one embodiment the selected analyte is glucose. In this embodiment the glucose may be detected, for example, by the use of glucose oxidase catalyzed oxidation of glucose to gluconic acid and hydrogen peroxide. Hydrogen peroxide, upon contact with a sensing electrode, releases electrons thereby creating an electric current that can be detected and correlated to the amount of glucose transported into the hydrogel.

The present invention also includes methods of making or manufacturing the hydrogels described herein, as well as components that comprise the hydrogels, for example, an electrode assembly, a collection assembly and/or collection assembly/electrode assembly (e.g., an AutoSensor) for use in an analyte monitoring device.

For example, in one aspect the present invention relates to collection assemblies/electrode assemblies comprising, a first hydrogel having first and second surfaces, the hydrogel comprising water, a hydrophilic compound capable of forming a gel in the presence of water, an electrolyte, a phosphate buffer present at a concentration of between about 125 mM and about 500 mM, and a pH of between about pH 6.5 to about pH 8.5, and a first iontophoretic electrode, wherein the first iontophoretic electrode is aligned to contact the second surface of the first hydrogel. Electrode assemblies may further comprise a first sensing electrode, wherein the first sensing electrode is aligned to contact the second surface of the first hydrogel. In one embodiment, the sensing electrode comprises a reactive surface comprising a platinum group metal (e.g., platinum on graphite) and a polymer binder. Electrode assemblies may further comprise a second hydrogel having first and second surfaces, and a second iontophoretic electrode, wherein the second iontophoretic electrode is aligned to contact the second surface of the second hydrogel. The second hydrogel may comprise, for example, water, a hydrophilic compound capable of forming a gel in the presence of water, an electrolyte, a phosphate buffer present at a concentration of between about 125 mM and about 500 mM, and a pH of between about pH 6.5 to about pH 8.5. Further, the electrode assembly may comprise a second sensing electrode, wherein the second sensing electrode is aligned to contact the second surface of the second hydrogel. Collection assemblies/electrode assemblies may also comprise liners, for example, interposed between the hydrogels and the electrodes and/or in contact with the first surface of the hydrogels.

In yet another aspect the present invention relates to collection assemblies/electrode assemblies comprising a first hydrogel having first and second surfaces, the hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5, and a first sensing electrode, wherein the first sensing electrode (i) comprises a reactive surface (e.g., comprising a platinum-group metal), and (ii) the reactive face is aligned to contact the second surface of the first hydrogel. Electrode assemblies may further comprise a first iontophoretic electrode, wherein the first iontophoretic electrode is aligned to contact the second surface of the first hydrogel. Further, the electrode assemblies may include a second hydrogel having first and second surfaces, and a second sensing electrode (i) comprises a reactive surface (e.g., comprising a platinum-group metal), and (ii) the reactive face is aligned to contact the second surface of the second hydrogel, as well as a second iontophoretic electrode, wherein the second iontophoretic electrode is aligned to contact the second surface of the second hydrogel. Collection assemblies/electrode assemblies may also comprise liners, for example, interposed between the hydrogels and the electrodes and/or in contact with the first surface of the hydrogels.

In another aspect, the present invention includes methods of making/manufacturing a collection assembly, for use in an analyte monitoring device (e.g., comprising an iontophoretic sampling device) useful to monitor a selected analyte or derivatives thereof present in a biological system. In one such method, first and second collection inserts are provided wherein each insert comprises a hydrogel having first and second surfaces, each hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5. A mask is provided wherein the mask comprises (i) a material that is substantially impermeable to the selected analyte or derivatives thereof, and (ii) inner and outer faces, wherein the mask defines first and second openings and a border. Further, a retaining layer is provided wherein the retaining layer comprises inner and outer faces, and the retaining layer defines first and second openings and a border. In the method, the inner face of the mask is positioned in facing relation with the first surface of each collection insert, such that (i) the first and second openings of the mask are, respectively, aligned with the first and second collection inserts (ii) each opening of the mask exposes at least a portion of the first surface of the collection insert with which it is aligned, and (iii) the border extends beyond the first surface of each of the collection inserts to provide an overhang. The inner face of the retaining layer is positioned in facing relation with the second surface of each collection insert, such that (i) the first and second openings of the retaining layer are, respectively, aligned with the first and second collection inserts, (ii) each opening of the retaining layer exposes at least a portion of the second surface of the collection insert with which it is aligned, and (iii) the border extends beyond the first surface of each of the collection inserts to provide an overhang. This method results in production of a collection assembly. In some embodiments the collection assembly is used to monitor glucose present in the biological system. In this case the hydrogels typically comprise glucose oxidase.

In yet another aspect the present invention relates to a method of making/manufacturing a collection assembly/electrode assembly (e.g., an AutoSensor) for use in an analyte monitoring device (e.g., comprising an iontophoretic sampling device) useful to monitor a selected analyte or derivatives thereof present in a biological system. In the method, first and second collection inserts are provided where each insert comprising a hydrogel having first and second surfaces, each hydrogel comprising a hydrophilic compound capable of forming a gel in the presence of water, an electrolyte, a phosphate buffer present at a concentration of between about 125 mM and about 500 mM, and a pH of between about pH 6.5 to about pH 8.5. A mask is provided that is (i) a substantially planar material that is substantially impermeable to the selected analyte or derivatives thereof, and (ii) inner and outer faces, wherein the mask defines first and second openings and a border. A retaining layer is also provided, where the retaining layer comprises inner and outer faces. The retaining layer also defines first and second openings and a border. First and second electrode assemblies are also provided, each electrode assembly comprising (i) first and second surfaces, and (ii) the first surface comprising an electrode. A support tray is also provided. The inner face of the mask is positioned in facing relation with the first surface of each collection insert, such that (i) the first and second openings of the mask are, respectively, aligned with the first and second collection inserts, (ii) each opening of the mask exposes at least a portion of the first surface of the collection insert with which it is aligned, and (iii) the border extends beyond the first surface of each of the collection inserts to provide an overhang. The inner face of the retaining layer is positioned in facing relation with the second surface of each collection insert, such that (i) the first and second openings of the retaining layer are, respectively, aligned with the first and second collection inserts, (ii) each opening of the retaining layer exposes at least a portion of the second surface of the collection insert with which it is aligned, and (iii) the border extends beyond the first surface of each of the collection inserts to provide an overhang. The first and second electrode assemblies are positioned relative to the outer face of the retaining layer such that a first surface of the electrode of the first electrode assembly is aligned with the first opening in the retaining layer, and a first surface of the electrode of the second electrode assembly is aligned with the second opening in the retaining layer. The support tray is positioned such that it contacts the second surface of each electrode assembly. This method results in production of a collection assembly/electrode assembly. In some embodiments the collection assembly/electrode assembly is used to monitor glucose present in the biological system. In this case the hydrogels typically comprise glucose oxidase.

In another aspect, the present invention relates to a collection reservoir system for providing containment of a sample comprising an extracted analyte. The collection reservoir system may, for example, comprise one or more collection reservoirs, wherein at least one collection reservoir comprises an ionically conductive material comprising an electrolyte, a phosphate buffer present at a concentration of between about 125 mM and about 500 mM, and a pH of between about pH 6.5 to about pH 8.5. The phosphate buffer may be present, for example, at a concentration of about 200 mM or 300 mM. The collection reservoir system may comprise further components as described herein (e.g., hydrophilic polymer). In one embodiment, each collection reservoir is in contact with an iontophoretic electrode for extraction of the target analyte. In another embodiment, each collection reservoir is in contact with a sensing electrode for detection of analyte amount or concentration. Further, each collection reservoir may be in contact with both an iontophoretic electrode and a sensing electrode.

The collection reservoir systems comprising ionically conductive materials of the present invention can be used in devices, for example, that employ transdermal extraction for the detection and/or quantification of analyte in a subject. The present invention also includes methods of making or manufacturing the collection reservoir systems described herein, as well as components which comprise the collection reservoir systems, for example, collection reservoirs associated with electrode assemblies. For example, in one aspect, the present invention includes methods of making/manufacturing collection reservoir systems comprising ionically conductive materials of the present invention for use in an iontophoretic sampling device useful to monitor a selected analyte or derivatives thereof present in a biological system. In the method, one or more collection reservoirs is provided and to at least one collection reservoir is added an appropriate volume of an ionically conductive material, comprising, electrolyte, and phosphate buffer present at a concentration of between about 125 mM and about 500 mM, with a pH of between about pH 6.5 to about pH 8.5.

In yet another aspect of the invention, a method of increasing transdermal flux of an analyte is described. In the method, the analyte is extracted across a tissue surface using an iontophoretic sampling device, wherein the sampling device comprises a hydrogel composition or collection reservoir system comprising ionically conductive material as described herein. The increase in transdermal flux is evaluated relative to extracting the analyte using the iontophoretic sampling device wherein the hydrogel composition instead comprises a hydrophilic compound capable of forming a gel in the presence of water, an electrolyte, a phosphate buffer present at a concentration of equal to or less than 100 mM, and a pH of about pH 7 to about pH 8. In one embodiment the tissue surface is the stratum corneum of skin tissue. In another embodiment the tissue surface is a mucosal surface. In one embodiment the analyte is glucose.

Yet another aspect of the invention includes a method of determining the concentration of an analyte in a mammalian subject using a monitoring system comprising an iontophoretic sampling device. In the method, a first surface of a hydrogel or collection reservoir system described herein is contacted with a tissue surface of the mammalian subject, wherein (i) a second surface of the hydrogel is in contact with a first iontophoretic electrode and a first sensing electrode, and (ii) the monitoring system comprises an electrode assembly, the electrode assembly comprising the first iontophoretic electrode, the first sensing electrode, and a second iontophoretic electrode. A current is provided to the first and second iontophoretic electrodes in an amount sufficient to effect the extraction of the analyte through the mammalian subject's skin, into the hydrogel and to the catalytic surface of the first sensing electrode. A potential is provided to the first sensing electrode in an amount sufficient to drive electrochemical detection of the analyte or an analyte-related chemical signal. Electrical current, generated by the electrochemical detection at the electrode, is measured. The measured current is then correlated to a concentration or amount of analyte in the mammalian subject. In one embodiment the analyte is glucose.

The tissue surface may, for example, be the stratum corneum of skin tissue or a mucosal surface. When the analyte is glucose, the hydrogel or collection reservoir system typically comprises glucose oxidase and the analyte related chemical signal is hydrogen peroxide.

The chemical characteristics of the hydrogel compositions and collection reservoir systems comprising ionically conductive materials of the present invention typically are such that non-specific, unintentional degradation or deterioration of the analyte being measured (or a chemical signal related to the amount or concentration of analyte) does not significantly affect accurate measurement of analyte amount or concentration in a sample.

2.2.0 Components of the Compositions of the Present Invention 2.2.1 Hydrophilic Polymers The hydrogel compositions of the present invention are produced using a hydrophilic compound capable of forming a gel in the presence of water. The hydrophilic compound can be polymers and/or co-polymers, wherein the polymers and/or co-polymers may additionally be cross-linked. Collection reservoir assemblies of the present invention may also comprise the ionically conductive materials described herein.

The polymer may comprise, for example, repeating units derived from a carboxy vinyl monomer, a vinyl ester monomer, an ester of a carboxy vinyl monomer, a vinyl amide monomer, a hydroxy vinyl monomer, a cationic vinyl monomer containing an amine or a quaternary ammonium group. The monomers can be used to make the polymers or co-polymers by methods known in the art. Exemplary hydrophilic polymers useful in the practice of the present invention include, but are not limited to, polyethylene oxide (PEO), polyvinyl alcohol, polyacrylic acid, polyvinyl pyrrolidone (PVP), or co-polymers of one or more polymers.

The polymers useful in the present invention typically have molecular weights of about 200 kD to about 1,500,000 kD (e.g., one such polymer is PEO Mr 600,000). The hydrophilic polymer may be present at a concentration of between about 0.5% to about 40%, preferably about 1% to about 35%, more preferably about 2% to about 20% of the total weight of the hydrogel. In a preferred embodiment the hydrophilic compound comprises polyethylene oxide (e.g., at about 8% to about 12% of the total weight of the hydrogel for PEO Mr 600,000). In one embodiment the hydrophilic compound consists essentially of polyethylene oxide (e.g., between about 9% to about 11% of the total weight of the hydrogel for PEO Mr 600,000).

In another aspect, the polymers for use in the hydrogels of the invention are cross-linked. The polymers can be cross-linked by the use of irradiation, by chemical means, or by mechanical means. Typically, the present hydrogels are obtained by exposing an aqueous mixture of the polymer, such as PEO, to a dose of radiant energy effective to cross-link the polymer, as described in U.S. Pat. No. 4,699,146. The source of the radiant energy suitable for cross-linking includes, but is not limited to, X-ray, gamma and beta rays, electron beam radiation, accelerated high energy electrons, ultraviolet, infrared, and the like.

Cross-linking of the hydrophilic polymer (with or without addition of specific cross-linking agents) is typically carried out to provide a hydrophilic compound having a swell ratio (wet) of about 4.0 to about 9.0, preferably of about 4.5 to about 8.5. The swell ratio (wet) is determined essentially as follows. The hydrogel is weighed and placed in water for a period of time sufficient to allow saturation of the polymer matrix by water. The saturated hydrogel is then weighed. The swell ratio (wet) is equal to the weight of the saturated hydrogel divided by the weight of the original hydrogel.

Cross-linking agents that are used to facilitate cross-linking when used in combination with radiation are disclosed within U.S. Pat. Nos. 4,684,558 and 4,989,607. Useful cross-linking agents for use with ultra violet radiation include N,N'-methylenebisacrylamide, polypropylene glycol monomethacrylate, polypropylene glycol monoacrylate, polyethylene glycol (600) dimethacrylate, triallylisocyanurate (TAIC), diallylisocyanurate (DAIC), polyethylene glycol (400) diacrylate, SR 415 ethoxylated trimethylolpropane triacrylate, SR 9035 ethoxylated trimetholpropane triacrylate. In addition, a photoinitiator maybe used, such as, for example, Esacure® (Lamberti s.p.a., Gallarate (VA), Italy) KB1 benzyldimethyl ketal, Esacure® TZT trimethylbenzophenone blend, Esacure® ITX isopropylthioxanthone, Esacure® EDB ethyl4-(dimethylamino) benzoate, and BP benzophenone. Gamma radiation and e-beam radiation cross-linking agents useful in the invention include, but are not limited to, ethylene glycol methacrylate, triethyleneglycol methacrylate, trimethylolpropane trimethacrylate (Sartomer® 350, Sartomer Company, Exton Pa., USA), and N,N'-methylenebisacrylamide. Thermal and chemical cross-linking agents useful in the invention include, but are not limited to, ethylene glycol methacrylate, triethylene glycolmethacrylate, trimethylolpropane trimethacrylate (Sartomer® 350), N,N'-methylenebisacrylamide, and glutaraldehyde. Typical gelatin, polyvinyl acetate, certain polyesters and calcium salts are used as chemical cross-linking agents. In addition, useful free radical initiators of cross-linking include, but are not limited to, azobisisobutyronitrile (AIBN), and peroxides, such as benzoyl peroxide.

Typically, cross-linking agents may be present in a hydrogel formulation from 0% to about 2% of the total weight of the hydrogel, preferably between about 0.001% to about 2%, more preferably 0.002% to about 1% of the total weight of the hydrogel. One preferred cross-linking agent is N,N'-methylenebisacrylamide.

2.2.2 Buffer Systems

The term buffer is used herein to refer to the components of the hydrogels or ionically conductive materials described herein used to maintain the pH within a defined range (typically about pH 6.5 to about pH 8.5, preferably between about pH 7 to about pH 8). The buffer includes a weak acid and its conjugate weak base whose pH changes only slightly on the addition of acid or alkaline substances. The weak acid becomes a buffer when alkali is added and the weak base becomes a buffer on addition of acid. This buffering action can be summarized by the following reaction:

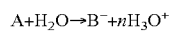

wherein n is a positive integer and $B^-$ is a weak base and A is a weak acid. The base B is formed by the loss of a proton from the corresponding acid A. The acid may also contain cations such as $NH_4^+$, a neutral molecule such as $CH_3COOH$, or an anion such as a monobasic phosphate anion. When alkali is added, hydrogen ions are removed to form water, but, as long as the added alkali is not in excess of the buffer acid, many of the hydrogen ions are replaced by further ionization of A to maintain the equilibrium. When acid is added, this reaction is reversed as hydrogen ions combine with the base B to form the acid A. A variety of different buffers can be used in connection with the present invention (in a preferred embodiment the buffer is a phosphate buffer) present in amounts sufficient to maintain the pH of the hydrogel in a range of about pH 6 to about pH 8.5, more preferably about pH 7 to about pH 8. Further, phosphate buffer concentration in the hydrogels or ionically conductive materials used in the collection reservoir assemblies of the present invention is typically between about 125 mM to about 500 mM, preferably between about 150 mM to about 300 mM. The phosphate buffer present in the hydrogels may comprise monobasic and dibasic phosphate. The monobasic and dibasic phosphate each typically comprise phosphate and counter ions. The counter ions are, for example, sodium counter ions, potassium counter ions, or a mixture thereof. Typical phosphate buffer systems include, but are not limited to, $NaH_2PO_4/Na_2HPO_4$, $KH_2PO_4/K_2HPO_4$, and mixtures thereof.

A buffer component of the present invention may function as a buffer as well as an electrolyte, without the addition of an additional electrolyte. An electrolyte is typically added to the hydrogel mixture or ionically conductive materials for use in a collection reservoir system such that the ionic strength of the gel or ionically conductive material is sufficient to produce acceptable electrical conductive properties. When an enzyme is used, e.g., glucose oxidase, the buffer maintains the pH within a range such that the enzyme remains relatively stable and optimally active. Typically, the pH range is maintained near neutral to help avoid skin irritation in that the hydrogels or ionically conductive materials for use in collection reservoir systems of present invention are held in contact with the skin surface. Further, by stabilizing the pH the flux of analyte across skin surface (tissue surface, muscosal membrane surface, etc.) into the hydrogel or collection reservoir assembly, comprising ionically conductive materials, will not be erratic over time.

2.2.3 Electrolytes

The hydrogels or collection reservoir systems, comprising ionically conductive materials, of the present invention typically have electrolytes in amounts sufficient to produce acceptable electrical conductive properties. The electrolytes can be, for example, ionizable inorganic salts, organic compounds, or combinations of both. Typical electrolytes include, but are not limited to, ammonium sulfate, monoethanolamine acetate, diethanolamine acetate, sodium lactate, sodium citrate, sodium chloride, magnesium sulfate, calcium sulfate, ammonium acetate, magnesium chloride, magnesium acetate, potassium lactate, potassium citrate, potassium chloride, or combinations thereof. Exemplary chloride salts include, but are not limited to, sodium chloride, potassium chloride, or a mixture thereof. The preferred electrolytes are chloride salts, e.g., potassium chloride, sodium chloride, or mixtures thereof, with sodium chloride being most preferred for particular embodiments as described herein. The electrolyte may be present in any amount, for example, at a concentration of about 0.1% to about 15% of the total weight of the hydrogel. A preferred range for chloride salt concentration is, for example, about 0.25% to about 2% of the total weight of the hydrogel. Typically the concentration of sodium chloride in the hydrogel is about 0.9%, i.e., comparable to chloride concentration typically present in biological fluids. Further, in collection reservoir systems, comprising ionically conductive materials of the present invention, the electrolyte may be present in any amount, preferable at a concentration of about 0.1% to about 15% of the total weight of the ionically conductive materials used in each reservoir.

When potassium phosphate salts are being used for the buffer and the buffer concentration is equal to or above about 200 mM, sodium chloride is typically used as the electrolyte.

2.2.4 Enzymes

The hydrogels or collection reservoir systems, comprising ionically conductive materials, of the present invention may contain an enzyme that is capable of catalyzing a reaction useful in the detection of the analyte of interest. The choice of the enzyme depends on the analyte to be detected and the detection system used. The concentration of the enzyme present in the hydrogel or collection reservoir system is related to the amount of analyte that is being detected. Some exemplary analytes and enzyme systems are described below (see, Section 4.0, Exemplary Analytes and Enzymes).

One exemplary analyte is glucose. When glucose is chosen as the molecule to be detected, an exemplary suitable enzyme for use in the present hydrogel or collection reservoir system, comprising ionically conductive materials, is glucose oxidase (GOx) which oxidizes glucose to gluconic acid and hydrogen peroxide. The subsequent detection of hydrogen peroxide on an appropriate electrode generates two electrons per hydrogen peroxide molecule that create a current which can be detected and correlated to the amount of glucose entering the hydrogel or collection reservoir comprising ionically conductive materials. This amount can be ultimately correlated to the amount of glucose present in the subject being monitored.

The glucose oxidase is typically present in an amount of from about 10 units to about 20,000 units or more per gram of the hydrogel or per gram of ionically conductive material present in a reservoir of a collection reservoir system, preferably between about 100 units to 5,000 units per gram. Glucose oxidase activity can be assayed, for example, essentially as described by Bergmeyer, H. U. in Methods in Enzymatic Analysis, 3 rd Edition (1983), Vol II, p. 201–203. Typically about 2000 units of glucose oxidase is added per gram of hydrogel component mixture (i.e., approximately 0.5% w/w powder in mix). As will be apparent to one of skill in the art, in some applications, it is desirable to include excess amounts of enzyme in order to ensure that all the glucose is readily broken down into gluconic acid and hydrogen peroxide.

In one embodiment, the hydrogel comprises an enzyme composition comprising glucose oxidase, wherein the glucose oxidase present in an amount of from about 10 units to about 5,000 units per gram of the total weight of the hydrogel. As described above, the glucose oxidase can be used to catalyze a reaction between glucose and oxygen resulting in the generation of hydrogen peroxide. Accordingly, when hydrogen peroxide detection is employed the hydrogen peroxide degradative components of the components (e.g., enzyme(s)) of the compositions of the present invention are reduced such that quantitation of hydrogen peroxide produced by the glucose oxidase reaction is not compromised.

The glucose oxidase enzyme may be obtained from natural sources or prepared recombinantly. When used for detection of glucose, the glucose oxidase can catalyze a reaction, for example, between glucose and oxygen resulting in the generation of hydrogen peroxide. Accordingly, hydrogen peroxide degradative components of the enzyme composition are preferably reduced such that quantitation of hydrogen peroxide produced by the glucose oxidase reaction is not compromised. Methods of preparing suitable glucose oxidase compositions are known in the art (see, e.g., Kalisz, H. M., et al., J. Chromatography 521:245–250, 1990; Welfle, K., et al., Studia Biophysica 138:245–260, 1990). The glucose oxidase enzyme can be commercially obtained from Biozyme (San Diego, Calif.), Genzyme (Cambridge, Mass.), Genencor (Rochester, N.Y.), Calzyme (San Luis Obispo, Calif.), Toyobo (Osaka, Japan) or any other commercial source.

Purity of enzyme compositions, for example, glucose oxidase, is important for keeping electrochemical background low (e.g, under 100 nanoamperes (nA)).

However, other enzymes could also be used provided they catalyze a reaction with an analyte of interest resulting in the generation of a detectable product in proportion to the amount of the molecule (e.g., see Section 4.0, Exemplary Analytes and Enzymes). The enzyme is typically present in an amount such that the rate limiting step in detection of the analyte is the rate at which analyte is transported into the hydrogel.

2.2.5 Humectants

In some embodiments the hydrogel compositions or collection reservoir systems, comprising ionically conductive materials, of the present invention may also comprise a humectant. For example, in the hydrogels of the present invention a humectant may be included from about 5 to 40 weight percent, preferably about 15 to about 25 weight percent humectant, for example, hexylene glycol and glycerol. The humectant is useful in slowing down the overall drying of the hydrogel. Other useful humectants include, but are not limited to, propylene glycol, sorbitol, poly(ethylene) glycol preferably having a molecular weight in the range of about 200 to 20,000, or polypropylene glycol preferably having a molecular weight in the range of about 500 to 5,000. Other humectants will be well-known to one skilled in the hydrogel art.

Examples of humectants that can be used in the invention include but are not limited to glycerol, propylene glycol, hexylene glycol, poly-(ethylene glycol), N-methylpyrrolidone, N-ethyl pyrrolidone, diacetone alcohol, γ-butyryl lactone, ethyl lactate, low molecular weight polyethylene glycol, or combinations thereof. Other humectants which may be employed include mono and di-saccharides such as glucose glutamate, and the like; castor oil and its derivatives, related stearates, oleates, and salts thereof; mixtures of saccharides and sugars; vegetable oil extracts such as mono-ethanolamine and amide derivatives from esters, triglycerides, as well as fatty acids of vegetable oils. Other oily, high molecular weight, high vapor pressure liquids which are biocompatible and which can be solubilized or dispersed in water also may be used as humectants. Preferably, the humectant used in the present invention is biocompatible.

2.2.6 Biocides

The hydrogels or collection reservoir systems, comprising ionically conductive materials, of the present invention may also comprise a biocide. Biocide is a substance that kills or inhibits the growth of microorganisms such as bacteria, viruses, molds, slimes, fungi, etc. A biocide may be a material which is also toxic to humans but is preferably a material which, when used in relatively low concentrations in a hydrogel or collection reservoir system does not cause skin irritation or any adverse effects on a human patient. Biocide chemicals include compounds such as chlorinated hydrocarbons, organometallics, hydrogen releasing compounds, metallic salts, organic sulfur compounds, quaternary ammonium compounds, phenolics, methyl parabens and the like. For example, if a biocide compound is used in connection with the present invention the amount is less than 0.5%–5% by weight or less based on the weight of the hydrogel material.

Preferred biocides include, but are not limited to, the following: chlorinated hydrocarbons; organometallics; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

One biocide used in the practice of the present invention is undecylenic acid. Undecylenic acid (10-undecenoic acid, or UA) is an unsaturated fatty acid. Both the acid form ("undecylenic acid") and the salt forms ("undecylenates") have biocidic activity, and may be used in combination with one another (or with other biocides). The biocide is commonly referred to herein as "undecylenic acid" without differentiation between the acid and salt forms. The salt forms may include but are not limited to the sodium, calcium and zinc salts. In addition, other esters of undecylenate, including but not limited to the methyl, ethyl, propyl, isopropyl, glyceryl, benzyl, allyl and epoxypropyl esters, are effective as biocides. When used as a biocide in the hydrogels of the present invention, the undecylenate biocide (acid, salt or mixture thereof) is present in the hydrogel at a concentration high enough to be effective as a biocide, for example between about 0.001 wt % and about 10 wt %, preferably between about 0.01 wt % and about 5 wt %, more preferably between about 0.1 wt % and about 2 wt %. In this embodiment the concentration of undecylenic acid is typically in the range of about 0.05% to 0.5% W/W of the total hydrogel weight, for example, about 0.2% w/w.

2.2.7 Structural Supports

The hydrogels of the invention can additionally include a layer of material of fibers or a non-woven fabric that is embedded within the hydrogel. The non-woven material aids in improving the structural integrity of the device. The material layer can be designed so that it provides a high degree of structural integrity to the hydrogel without adversely effecting the flow of current through the gel. The hydrogels may further include a structural support which is embedded in the gel, which support includes, but is not limited to, a woven fabric, a non-woven fabric, dispersed fibers, or a membrane. In addition it is possible to include a membrane which aids in filtering out undesirable materials which are drawn into the hydrogel. This structural support is embedded in the gel and preferably has a size and configuration which matches that of the hydrogel patch. A variety of different materials can be used to provide the structural support. Useful non-woven fabrics include those sold as Reemay 2200, 2000 and 2400 series (Remay Inc., TN). The layer may be spun bonded polyester which may be straight or crimped fibers. It is possible to use super absorbent fibers or fabrics. Commercially available materials include Du Pont Sontara™ (E.I. du Pont de Nemours and Company, Wilmington, Del.) (polyester blend fabrics), Delnet™ (Del-Star Technologies, Del.) fabric, and Reemay series (Remay Inc., TN). Preferred structural supports include Reemay series fabrics and Delnet fabrics. Open-cell and closed-cell materials can be used.

2.2.8 Exemplary Hydrogel Formulations

Some exemplary hydrogel formulations are set forth in Example 1. Typically, the hydrogels are comprised of a hydrophilic compound that forms a material that holds water in place and allows the flow of electrical current. The compound may be an absorbent material, porous material or polymers that may be cross-linked to form a porous network of interconnected cells or a solute which forms a gel with water. The solute or solid material component of the gel is generally present in an amount of about 0.5% or more and preferably less than 40% by weight based on the total weight of the hydrogel. The water, and the hydrogel as a whole, is made electrically conductive by the inclusion of an electrolyte such as NaCl and/or KCl. The hydrogel may also comprise an enzyme, which catalyzes a reaction such as a reaction with glucose allowing for the formation of hydrogen peroxide in water and ultimately generating the release of two electrons per molecule of glucose. Glucose drawn into the hydrogel is oxidized to gluconic acid and hydrogen peroxide with the aid of the GOx, resulting in electrons being released that can be detected and related to the amount of glucose entering the hydrogel.

The hydrogel is also preferably comprised of a buffer that maintains the pH of the hydrogel in the range of from about 3 to 9, and may be further comprised of a cross-linking agent, a biocide, and a humectant. In one embodiment of the present invention, when higher phosphate buffer concentrations are used (e.g., between about 125 mM and 500 mM), for example, to increase analyte flux and/or to increase the mutarotation rate of the analyte, potassium salts of phosphate buffers are preferred in hydrogel formulations. Higher phosphate concentration, for example, in hydrogels comprising PEO is typically not possible using only sodium phosphate salts due to their insolubility at lower temperatures and high concentrations. Potassium phosphate salts are more soluble in solution at a given temperature and concentration than the corresponding sodium salts. Experiments performed in support of the invention demonstrated that the replacement or combination of sodium phosphate salts with potassium phosphate salts allows the phosphate concentration to be increased while maintaining the stability of the salts in the solution phase of a hydrogel.

The hydrogel is typically in the form of a thin, flat disc which will conform to the contours of human skin and may have a non-woven fabric or porous membrane (for example, Delnet™ fabric) embedded therein. The concentration of the buffer and the pH is chosen such that, for example, the observed analyte-related current is maximized within a measurement cycle.

In one aspect of the present invention, the hydrogels comprise: a phosphate buffer at a concentration of between about 125 mM and about 500 mM, preferably between about 150 mM and 300 mM; a pH of between about pH 6.5 to about pH 8.5, preferably between about pH 7 to about pH 8; an electrolyte at a concentration of between about 0.1% to about 10% of the total hydrogel weight (for example, a concentration of chloride ion of 17 mM to 1.7 M); a hydrophilic polymer at between about 0.5% to about 40%, preferably about 1% to about 35%, more preferably about 2% to about 20% of the total weight of the hydrogel; a cross-linking agent between about 0% to about 2% of the total weight of the hydrogel, one or more enzymes; and between about 45% to about 90% water. Other components may include, but are not limited to, wetting agents (e.g., hexylene glycol), humectants, biocides, and structural supports. Water makes up the weight percent of the hydrogel to 100% after addition of all other components. Further, hydrogels of the present invention may be cross-linked using, for example, electron beam radiation or UV radiation.

For formation of hydrogels, the minimum concentration of hydrophilic polymer is typically dependent on the molecular weight range (Mr) of the polymer(s) being used. A minimum concentration is one generally sufficient to provide structural integrity to the hydrogel. The minimum concentration of hydrophilic polymer can be very low when the composition of the present invention is being used as an ionically conductive material to fill a collection reservoir, that is, in the situation where it is not necessary for the material to maintain its own shape.

The hydrogels of the present invention are typically, substantially planar and have a thickness in a range of about 1 mil to about 60 mils, preferably about 1 mil to about 25 mils, more preferably about 5 mils to about 10 mils. In a preferred embodiment, the hydrogels have first and second surface areas, and each surface area is in a range of about 0.5 $cm^2$ to about 10 $cm^2$, more preferably between about 0.5 $cm^2$ to about 2.25 $cm^2$, and the hydrogel has a thickness from about 1 mil to about 10 mils. In a preferred embodiment, a hydrogel disk is about ¾ inch in diameter +/−15% (i.e., 0.44 sq. in. +/−0.07 sq. in.) and has a thickness of about 7 mils +/−15% (i.e., 0.007 in. +/−0.00105 mils). Hydrogels may be of any shape suited to use in a particular analyte monitoring device. In a preferred embodiment, the hydrogel is essentially circular.

Ionically conductive materials for use in a collection reservoir system may have similar components as described herein with reference to hydrogels. In some embodiments the hydrophilic polymer may be omitted. In some embodiments use of hydrophilic polymer is at a low level that maintains a relatively fluid nature of the ionically conductive materials for use in the collection reservoir system. In some embodiments, the hydrophilic polymer may be present at concentrations that give structural integrity to the ionically conductive materials in the collection reservoir.

Characterization of the hydrogels or ionically conductive materials for use in a collection reservoir system of the present invention can be carried out using methods known to one of skill in the art in view of the teachings of the specification. Some exemplary characterizations are described herein below.

Although a number of methods and materials similar or equivalent to those described herein can be used in the practice of the present invention, some preferred materials and methods are described herein.

2.3.0 Electrical Conductivity

Low electrochemical reactivity is another characteristic of the compositions of the present invention (e.g., hydrogels or collection reservoirs comprising an ionically conductive material of the present invention). Low electrochemical reactivity refers to a low level of background electrical signal typically when the compositions of the present invention are in contact with a sensing electrode. Such a low level of signal improves the ability of the compositions of the present invention to be used for detection of small quantities of analyte. Preferably, the hydrogels and collection reservoirs comprising an ionically conductive material of the present invention create an electrical environment such that background noise created when the composition is used for analyte detection is as close to zero as possible. Preferably, the amount of background noise is less than 500 nA, more preferably less than 200 nA, and most preferably less than 50 nA when measured using a hydrogel of the present invention and a platinum electrode with a surface area of approximately 1 $cm^2$ measured at about 24° C. for an applied potential of 0.420V.

Background current (or noise) may be measured by the following procedure essentially as described in PCT International Publication WO/97/02811. A rectangular electrode assembly consisting of a sensing and a counter Pt electrode and a reference Ag/AgCl electrode is used. Exemplary platinum sensing electrodes and Ag/AgCl iontophoretic electrodes have been described in U.S. Pat. No. 6,587,705. An approximately ⅝ inch diameter hydrogel disk is prepared, one release liner is removed, and the disk is placed on a rectangular electrode assembly with the exposed hydrogel side in contact with the platinum electrode having a surface area of approximately 1 cm². The background current is measured for an applied potential of 0.420V. The measurements are carried out at about 24° C. The electrode is preconditioned at a bias potential of 0.75V for 10 minutes before starting the background current measurement. (This amount of preconditioning is not sufficient to remove all electroactive contaminants from the gel.) The background current measurement typically decays asymptotically to a steady background current within approximately 15 to 30 minutes. Measurements are taken at approximately 60 minutes. For the compositions of the present invention (e.g., hydrogels or collection reservoirs comprising an ionically conductive material of the present invention), background current is less than 500 nA, preferably less than 200 nA, more preferably less than 100 nA, and more preferably less than 50 nA. Most preferably, the background current of the hydrogel in combination with the platinum electrode, at equilibrium or steady-state, has a background current as close to 0 nA as possible.

The components used to formulate hydrogel compositions of the present invention may be treated to remove compounds that contribute to background electrical signal. For example, antioxidants may be present in commercial polymers that are electroactive. Such electroactive compounds may be removed from the components of the present invention by a clean up procedure including, but not limited to, the following methods: rinsing, extraction, super-critical fluid extraction, diafiltration, size exclusion chromatography, dialysis, ion exchange chromatography, electrochemical preconditioning, and reverse phase chromatography.

The compositions (e.g., hydrogels or collection reservoirs comprising an ionically conductive material of the present invention) of the present invention must be electrical conductive and should have a resistance of less than approximately 20 kOhms, preferably less than approximately 10 kOhms, and more preferably less than 5 kOhms. Electrical resistance may be measured essentially as follows. Two 0.6 cm Ag/AgCl electrodes are placed 1 cm apart across a hydrogel sheet that is 10 mil (254 microns) thick. A known electrical potential is passed across the hydrogel. The conductivity of the hydrogel is measured using, for example, a multimeter (e.g., a Fluke 85 Multimeter). This test is typically carried out at 24° C. The resistance of the hydrogel is then calculated.

2.4.0 Gel Viscosity and Elasticity

The hydrogels of the invention preferably adhere to human skin and conform to the configuration of the skin over which they are applied. Thus the hydrogels will be flexible to the extent that it will adhere to skin and not fall off due to gravity. Further, when removed the hydrogels will not be sufficiently adhesive such as to tear away skin and they can be removed and will not adhere to the skin on being removed so as to leave a tactile hydrogel residue on the skin following removal.

One indication of gel elasticity are the swell ratios of dry versus wet hydrogels (i.e., for swell ratio (wet), a hydrogel is weighed, hydrated, then reweighed and the ratio is wet weight over original weight), and/or wet versus dry hydrogels (i.e., for swell ratio (dry), a wet hydrogel is weighed, desiccated, then reweighed and the ratio is dry weight to wet weight).

Hydrogels of the present invention typically have a swell ratio (wet) of about 4.0 to about 9.0, preferably of about 4.5 to about 8.5.

2.5.0 Performance

The hydrogels of the present invention exhibit structural integrity and stable electrical properties. The hydrogels of the present invention do not substantially exude water, are structurally unchanged and functional over the range of temperatures normal for physiological use, do not store electrical charge, and have low electrical resistance. In one embodiment of the present invention, the hydrogels also exhibit further superior properties in that they increase the flux of analyte across a tissue surface (e.g., the stratum corneum) and this could be used to reduce skin irritation. Further, the hydrogels of the present invention increase the rate of mutarotation of $\alpha$-glucose to $\beta$-glucose. The performance of the hydrogels can be determined, for example, as described in Examples 2 and 3.

2.5.1 Enhancement of Transdermal Flux

The term "flux" refers to the rate of transport of an analyte, e.g., glucose, across a tissue or mucosal surface, e.g., the corneum stratum of skin. Typically the analyte is collected in a collection reservoir, e.g., a hydrogel or an ionically conductive material contained within a well of a collection reservoir assembly. In the case of glucose being transdermally extracted into a hydrogel, flux refers to the transport of glucose over time per unit area of hydrogel ($nmol/cm^2/hr$).

Analyte flux may be evaluated for different conditions, for example, as follows. One or more collection reservoirs are placed on the skin surface of a subject. Each collection reservoir comprises a specific combination of components (e.g., a particular type of buffer, pH, buffer concentration, electrolytes, etc.). The analyte of interest is extracted across the skin surface of a subject (e.g., by the application of an electrical current for iontophoretic extraction). The amount or concentration of analyte extracted over a period of time is measured. The procedure is repeated on the same or different subjects, wherein specific components of the collection reservoir are varied. The amount of analyte extracted is then compared for the different conditions (i.e., the varied components of the collection reservoir). An exemplary flux analysis for glucose is presented in Example 2.

The results presented in Example 2 demonstrate that the flux of glucose from a human subject into the buffer contained in the collection reservoir can be increased by increasing the pH of the buffer (e.g., Example 2A, at pH 6, phosphate concentration 250 mM, flux was 0.69 $nmol/(cm^2\text{-}hr)$ versus, at pH 6.5, phosphate concentration 250 mM, flux was 1.25 $nmol/(cm^2\text{-}hr)$. The flux of glucose from a human subject into the buffer contained in the collection reservoir can be increased by increasing the total concentration of the phosphate buffer (e.g., Example 2A, at pH 6.5, phosphate concentration 125 mM versus 250 mM, flux was 1.15 vs. 1.25 $nmol/(cm^2\text{-}hr)$, respectively, and, at pH 7.5, phosphate concentration 50, 100, and 200 mM, flux was 2.09, 2.52, and 2.74 $nmol/(cm^2\text{-}hr)$, respectively). This result is surprising as increased ion concentration would be expected to compete with the available iontophoretic current to decrease flux at higher buffer concentration. Yet, flux was enhanced at higher buffer concentration.

The experiments described in Example 2B showed the effects of increased phosphate concentration in the hydrogel on the performance of an analyte monitoring device on a human subject. Two exemplary conditions were investigated: 100 mM sodium phosphate hydrogels and 200 mM potassium phosphate hydrogels (Delnet scrim for both conditions). Analyte sensitivity was much higher when the analyte monitoring device employed higher concentrations of phosphate buffer in the hydrogels (200 mM potassium phosphate versus 100 mM sodium phosphate hydrogels). The slope of the line of the signal from the analyte monitoring device, when plotted against reference blood values, provided a signal of 299 nC/(mg/dL) for 200 mM phosphate concentration versus a signal of 207 nC/(mg/dL) for 100 mM phosphate concentration. This is about a 30% enhancement of signal indicating increased sensitivity of measurement. This increase in sensitivity of the measurement can be attributed to increased skin flux and/or increased sensor sensitivity due to mutarotation due to the higher phosphate concentration.

The experiments described in Example 2C provide another example of the effect of increased phosphate concentration on analyte monitoring device performance. Four conditions were tested including 100 mM sodium phosphate hydrogels with Reemay scrim, and 300 mM potassium phosphate hydrogels with Delnet scrim. Analyte sensitivity of the electrode increased with increasing phosphate concentration from 100 to 200 mM phosphate (175 vs. 258 and 280 nC/(mg/dL)) and 100 to 300 mM phosphate (175 vs. 274 nC/(mg/dL)). The results of this experiment support the conclusion that increasing the hydrogel's phosphate concentration increases performance of the analyte monitoring device.

The experiments described in Example 2D also support that increasing the phosphate buffer concentration in the hydrogel results in improved performance of the analyte monitoring device that employs the hydrogels. Four phosphate buffer concentrations/ink formulation combinations were evaluated as follows: 1) Control (standard ink/100 mM sodium phosphate hydrogel with Delnet), 2) Standard ink/200 mM potassium phosphate hydrogel with Reemay, 3) Alternative ink formulation/100 mM sodium phosphate hydrogel with Delnet, and 4) Alternative ink formulation/200 mM potassium phosphate hydrogel with Reemay. Analyte sensitivity of the electrode increased with increasing phosphate concentration. The results of this experiment support the conclusion that increasing the hydrogel's phosphate concentration increases performance of the analyte monitoring device. Furthermore, Example 2D also shows data related to the effect of the four conditions on sensor sensitivity when not applied to a human subject. An increase in the observed percent recovery may be related to the increased rate at which mutarotation of glucose occurs. Accordingly, known amounts of glucose were spiked onto the AutoSensor and slightly higher recoveries were obtained when employing hydrogels with higher phosphate concentration. However, the increase was not nearly as large as the increase in sensor sensitivity when used for extraction of glucose on a human subject. The percent recovery in the spiking experiment went from 72% to 80% (Table 6, standard ink sensor, 100 mM phosphate to 200 mM phosphate) an increase of approximately 10%. This is attributable to mutarotation enhancement. The slope increase in the human study experiment went from 113 to 169 nC/(mg/dL) (Table 5) for the same conditions, an increase of approximately 50%. Thus, only approximately one-fifth of the increased detection of analyte (in this case glucose) is due to mutarotation and four-fifths of the increased detection is due to skin flux. The enhancement in signal when using the analyte monitoring system on a human subject, therefore, must be due primarily to enhanced skin flux and secondarily to enhanced mutarotation of α-glucose to β-glucose.

Thus, mutarotation of glucose was seen to increase in the hydrogel compositions of the present invention as evidenced by higher percent recovery of glucose in hydrogels having higher phosphate buffer concentrations. However, the increase in mutarotation rate does not account for the total increases seen in the above-described flux experiments suggesting that the phosphate buffer concentration is providing a good analyte flux improvement across the skin surface.

Incorporating a hydrogel of the present invention comprising a higher phosphate buffer concentration (i.e., greater than about 125 mM up to about 500 mM) provides several advantages for analyte extraction and detection when using an analyte monitoring device that employs electroosmotic extraction of analyte. First, analyte sensitivity (i.e., the amount of analyte detected by, for example, a biosensor electrode) is improved relative to hydrogels using lower concentrations of phosphate buffer (i.e., less than or equal to about 100 mM phosphate buffer concentration). This improved analyte sensitivity is in large part due to increased transdermal flux of the analyte when using the hydrogels of the present invention. Obtaining higher flux at a higher ionic strength while maintaining the same pH (for example, two phosphate buffer systems with the same pH, however in the buffer system with the higher phosphate buffer concentration ionic strength of the buffer is increased as well) is an unexpected result. Typically, an increase in ionic strength would be thought to reduce transdermal flux. When a high phosphate concentration buffer composition of the present invention is employed in iontophoretic extraction of glucose across a skin or mucosal surface, glucose flux into said buffer is typically at least about 0.65 nmol/cm$^2$hr, at least about 0.8 nmol/cm$^2$hr, at least about 1.0 nmol/cm$^2$hr, or at least about 1.1 nmol/cm$^2$hr, at 0.25–0.32 mA/cm$^2$ current density. Second, the increased phosphate concentration of the hydrogels of the present invention also improves the mutarotation rate of some analytes, for example, sugars. Third, experiments performed in support of the present invention suggest that the increased sensitivity results in fewer error associated signals (particularly in the context of calibration ratio skips and aborted calibrations) thus providing improved convenience for a user of an analyte monitoring system that employs the hydrogels or buffer systems of the present invention.

In order to obtain higher buffer concentrations in a hydrogel or ionically conductive materials for use in a collection reservoir system, experiments performed in support of the present invention suggest that use of a potassium salt of a phosphate buffer is generally better suited to the hydrogel formulation because the potassium salt phosphate buffers tend to remain soluble in the hydrogel or liquid formulations, particularly if the hydrogel or liquid formulation is to be refrigerated or may encounter cold temperatures during shipping. Accordingly, in a preferred embodiment of the hydrogel formulations of the present invention, potassium salts of phosphate buffers are preferred to sodium salts of phosphate buffers. Mixtures of potassium and sodium salts of phosphate buffers may also be employed.

2.5.2 Improved Clinical Performance of Analyte Monitoring Devices Using Higher Concentrations of Phosphate Buffer in a Collection Reservoir The collection reservoirs, comprising higher concentrations of phosphate buffer, of the present invention were used in clinical trials to confirm the efficacy and benefits of their use. The results of the clinical trials are presented in Example 3 and Example 4.

The clinical trial population consisted of 66 subjects (females and males), age 18 years and older, with type 1 or type 2 diabetes mellitus. The Cygnus GlucoWatch G2 biographers used in the clinical study were research versions of the device that were used to collect all of the raw data typically collected by a GlucoWatch G2 biographer; but the device performed no calculations based on the raw data. Emulator programs, which used baseline subtraction and carried out integration of current signal, were used to calculate nC results based on the nA signals. Although the results are described with reference to the GlucoWatch G2 biographer, the compositions and methods of the present invention may be applied to other analyte monitoring devices as well, in particular, those employing transdermal or transmucosal extraction of analyte.

The results presented in Example 3 demonstrate a significant advantage of using higher concentrations of phosphate buffer in a collection reservoir, for example, a hydrogel, for the detection of analyte, in that use of the high phosphate gels resulted in higher analyte sensitivity when using the high phosphate gels with sensing electrodes for electrochemical detection of analyte.

Further, CalRatio values for the different conditions were also evaluated. The CalRatio check provides a screen for valid or efficacious calibration readings (see, e.g., U.S. Pat. No. 6,326,160). The CalRatio screen may be employed in analyte monitoring devices, for example, the GlucoWatch G2 biographer. It has been previously determined that if the CalRatio falls outside of a preselected range of values, then the calibration should be rejected and the calibration redone. The clinical study data demonstrated that the high phosphate gels of the present invention performed better than the standard hydrogels (e.g., comprising 100 mM phosphate buffer), for example, showing reduced CalRatio values and overall improved analyte sensitivity attributable to the high phosphate hydrogel.

Example 4 presents data concerning the performance of collection reservoirs comprising higher concentrations of phosphate buffer, for example, a hydrogel, relative to failed calibration attempts and recalibration performance of standard phosphate buffer concentration (e.g., a hydrogel comprising a phosphate buffer concentration of 100 mM). Out of all GlucoWatch G2 biographers with the standard hydrogels that had a calibration attempt (60 GlucoWatch G2 biographers), 14 GlucoWatch G2 biographers had at least one failed attempt to calibrate. Out of all GlucoWatch G2 biographers with the high phosphate hydrogels that had a calibration attempt, 2 GlucoWatch G2 biographers had at least one failed attempt to calibrate. Eight GlucoWatch G2 biographers with the standard hydrogels had a maximum possible number of failed calibration attempts (four) and shut off. None of the GlucoWatch G2 biographers with the high phosphate hydrogel shut off due to failed calibration attempts. Out of a total of 61 calibration attempts for the G2 GlucoWatch G2 biographers with the high phosphate hydrogel, 58 (95%) resulted in a successful calibration. For the standard hydrogel, only 56% of calibration attempts were successful.

Most of the failed calibration attempts for GlucoWatch G2 biographer with the standard hydrogel were due to data integrity checks (e.g., a CalRatio check) implemented to ensure that the sensitivity of the system is sufficient to adequately measure glucose. The sizable reduction in percentage of failed calibration attempts (from 44% for the standard hydrogel to 5% for the high phosphate hydrogel, i.e. ~8 fold) was likely due at least in part to the larger signal produced by the high phosphate hydrogel.

Further, all of the GlucoWatch G2 biographers with the high phosphate hydrogel recalibrated successfully on the first try. With the standard hydrogel, out of seven GlucoWatch G2 biographers with recalibrations, five were able to recalibrate successfully on the first try and two had one unsuccessful recalibration attempt.

The clinical data presented in Example 4 demonstrate that use of the high phosphate hydrogels reduced the frequency of failed calibration of the GlucoWatch G2 biographer. Further, use of the high phosphate hydrogels improved recalibration attempts relative to use of a standard hydrogel (100 mM phosphate buffer).

The results of these experiments demonstrate the value of the high phosphate hydrogels of the present invention for use in analyte monitoring devices in a clinical environment. Accordingly, in one aspect of the present invention, higher concentrations of phosphate buffer in a collection reservoir, for example, a hydrogel, can assist in improving performance of an analyte monitoring device by, for example, improving analyte sensitivity, reducing failed calibration attempts, and improving recalibration efficiency.

2.5.3 Reduction of Skin Irritation

A further advantage of the present invention is the possibility of reducing skin irritation. Analyte sensitivity (i.e., the amount of analyte detected after extraction) is improved when using the hydrogels of the present invention relative to hydrogels using lower concentrations of phosphate buffer (i.e., less than or equal to about 100 mM phosphate buffer concentration). This improved analyte sensitivity appears to be in large part due to increased transdermal flux of the analyte when using the hydrogels of the present invention. The higher flux of analyte across, for example, the stratum corneum, allows for using a lower current density to get a suitable flux of analyte to provide an adequate amount of analyte for detection/sensing. Use of a lower current for analyte extraction helps to reduce skin irritation at the site of contact of the device and the subject being monitored.

Accordingly, in one aspect of the present invention, higher concentrations of phosphate buffer in a collection reservoir, for example, a hydrogel, can assist in reducing skin irritation.

2.5.4 Mutarotation

When the analyte of interest has two or more stereoisomeric forms, such as the anomeric forms of sugars which undergo mutarotation, and only one isomeric form of the analyte is detectable using a detection system, for example, electrochemical detection, then components may be added to the hydrogel to facilitate mutarotation to the detectable stereoisomeric form. This applies, for example, to sugars including but not limited to glucose.

For example, an aqueous solution of glucose contains α-glucose and β-glucose in an equilibrium. However, glucose oxidase is specific for β-glucose. Therefore, as the reaction proceeds, the concentration of β-glucose decreases and α-glucose mutarotates to maintain the equilibrium. The gradual mutarotation of α-glucose to β-glucose is manifested by delayed hydrogen peroxide formation, which may be carried over into the next measurement cycle. The purpose of increasing the mutarotation rate is to prevent the carryover of glucose to the next measurement cycle and to provide more accurate detection of glucose levels in a sample (e.g., including glucose originally present in the sample as both α-glucose to β-glucose). Carryover refers to the observation that not all glucose reacts within each measurement cycle. Thus, glucose can accumulate over time thereby decreasing the accuracy of results obtained in measurements occurring in later measurement cycles.

In addition, because a solution of glucose at equilibrium contains greater than 35% α-glucose, the signal with slow mutarotation is up to 35% lower than a signal from a sample with rapid mutarotation. More rapid mutarotation increases the signal to noise ratio.

Because a solution of glucose at equilibrium contains greater than 35% α-glucose, sensing times greater than 5 minutes may be required solely to determine the charge at the end of the reaction. Thus, an increased mutarotation rate is desirable because it (i) results in higher current values over a shorter measurement time period, (ii) results in higher signal to noise ratios, and (iii) reduces the recovery time thereby increasing the number of readings that can be taken over a given time interval.

The rate of mutarotation of α-glucose to β-glucose may be increased by, for example, by increasing the pH of the hydrogels or by increasing the concentration of the phosphate buffer.

Further, the hydrogels of the present invention can, in addition or alternatively, include histidine, imidazole, glutamic acid, aspartic acid, α-hydroxypyridine or mutarotase in order to increase the rate of mutarotation. These compounds are preferably present in a concentration of about 20 mmol to about 100 mmol and preferably do not substantially affect the activity of any enzyme that is present (e.g., GOx).

To increase the mutarotation rate of aαglucose to β-glucose phosphate buffer and mutarotase are preferably used either individually or in combination.

In one aspect, the hydrogels of the present invention comprise a mutarotase enzyme. Mutarotase may be present where the ratio of mutarotase: GOx is about 0.25–1:10. Thus, for example, about 0.4 units of mutarotase are used for 20 units of GOx, or about 15 units of mutarotase are used for 100 units of GOx. The enzyme can be commercially obtained from Biozyme (San Diego, Calif.), Genzyme (Cambridge, Mass.), Genencor (Rochester, N.Y.), Calzyme (San Luis Obispo, Calif.), Toyobo (Osaka, Japan) or any other commercial source.

In another aspect, the hydrogels of the present invention comprise a phosphate buffer at a concentration effective to increase the mutarotation rate of α-glucose to β-glucose. The phosphate concentration is about 125 mM to about 500 mM, preferably about 150 mM to about 300 mM. Thus, in one aspect the present invention includes hydrogels buffered at about pH 7 to about 8 with phosphate buffer present at concentrations of about 125 mM, about 150 mM, about 200 mM, about 250 mM, about 300 mM, up to and including about 500 mM, and all concentration values between about 125 mM to about 500 mM.

In addition, the buffer is included in order to maintain the pH of the hydrogel within a desired range, preferably in the range of about pH 4 to about pH 9, more preferably about 6 to about 8.5, or most preferably about 7 to about 8. The pH range is chosen such that (i) any enzyme in the hydrogel, e.g., glucose oxidase, remains relatively stable, (ii) skin irritation is minimized, and (iii) the flux of the analyte, e.g., glucose, through the skin and into the hydrogel is optimal.

3.0 Exemplary Monitoring Systems

Numerous analyte monitoring systems can be used with sensor elements made using the compositions of the present invention. Typically, the monitoring system used to monitor the level of a selected analyte in a target system comprises a sampling device, which provides a sample comprising the analyte, and a sensing device, which detects the amount or concentration of the analyte or a signal associated with the analyte amount or concentration in the sample.

One exemplary monitoring system (the GlucoWatch biographers) is described herein for monitoring glucose levels in a biological system via iontophoretic, transdermal extraction of glucose from the biological system, particularly an animal subject, and then detection of signal corresponding to the amount or concentration of the extracted glucose. Analyte monitoring systems (including the GlucoWatch biographers) and components thereof, have been previously described (see, for example, U.S. Pat. Nos. 6,398,562, 6,393,318, 6,370,410, 6,341,232, 6,391,643, 6,309,351, 6,299,578, 6,298,254, 6,272,364, 6,233,471, 6,180,416, 6,144,869, 6,023,629, 5,989,409, 5,771,890, 6,356,776, 6,326,160, 6,284,126, 6,139,718, 5,954,685, 6,201,979, 6,141,573, 5,827,183, 6,438,414, 6,529,755, 6,546,269, 6,594,514, 5,735,273, and 6,595,919; and PCT International Publication Nos. WO0218936, WO0217210, WO0215778, WO0215777, WO0188534, WO0188534, WO0064533, WO0047109, WO0024455, WO0018289, WO0015108, WO9958973, WO9958190, WO9958051, WO9958050, WO9842252, WO9724059, WO9710499, WO9710356, WO9702811, WO9600110, and WO9600109). The GlucoWatch biographer line of products includes, but is not limited to, the GlucoWatch® (Cygnus Incorporated, Redwood City, Calif.) biographer and the GlucoWatch® G2™ (Cygnus Incorporated, Redwood City, Calif.) biographer.

Using the GlucoWatch biographer, transdermal extraction is carried out by applying an electrical current to a tissue surface at a collection site. The electrical current is used to extract small amounts of glucose from the subject into a collection reservoir. The collection reservoir is in contact with a sensor element (e.g., a biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing a selected algorithm) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

To sample the analyte, one or more collection reservoirs are placed in contact with a tissue surface on a subject. The ionically conductive material, e.g., the hydrogels of the present invention, within the collection reservoir is also in contact with an electrode (for reverse iontophoretic extraction) which generates a current sufficient to extract glucose from the tissue into the collection reservoir. Referring to FIG. 1A, an exploded view of exemplary components comprising one embodiment of a collection assembly/electrode assembly (e.g., an AutoSensor) for use in an iontophoretic sampling system is presented. The AutoSensor components include two biosensor/iontophoretic electrode assemblies, 104 and 106, each of which have an annular iontophoretic electrode, respectively indicated at 108 and 110, which encircles a biosensor electrode 112 and 114 (such biosensor electrodes may comprise the compositions of the present invention). The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In an alternative embodiment, the electrode assemblies can include bimodal electrodes. A mask layer 128 may be present.

The mask and retaining layers are preferably composed of materials that are substantially impermeable to the analyte (e.g., glucose) to be detected. By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

In other embodiments, the collection reservoir layer may further comprises a gasket layer and wherein the gasket layer is between the mask layer and the retaining layer (see, for example, U.S. Pat. Nos. 6,393,318, 6,341,232, and 6,438,414).

In one embodiment, the mask layer and retaining layer each define at least one opening and at least a portion of a collection reservoir is exposed by each opening to provide a flow path through the collection assembly. Further, the collection reservoir may be defined by a corral or gasket that contains, seals, or retains the collection reservoir at a desired location. When a gasket is used the entire surface of the ionically conductive materials of the collection reservoir may be exposed, for example, using a mask layer that contacts the edges of the gasket.

Figure 1B:
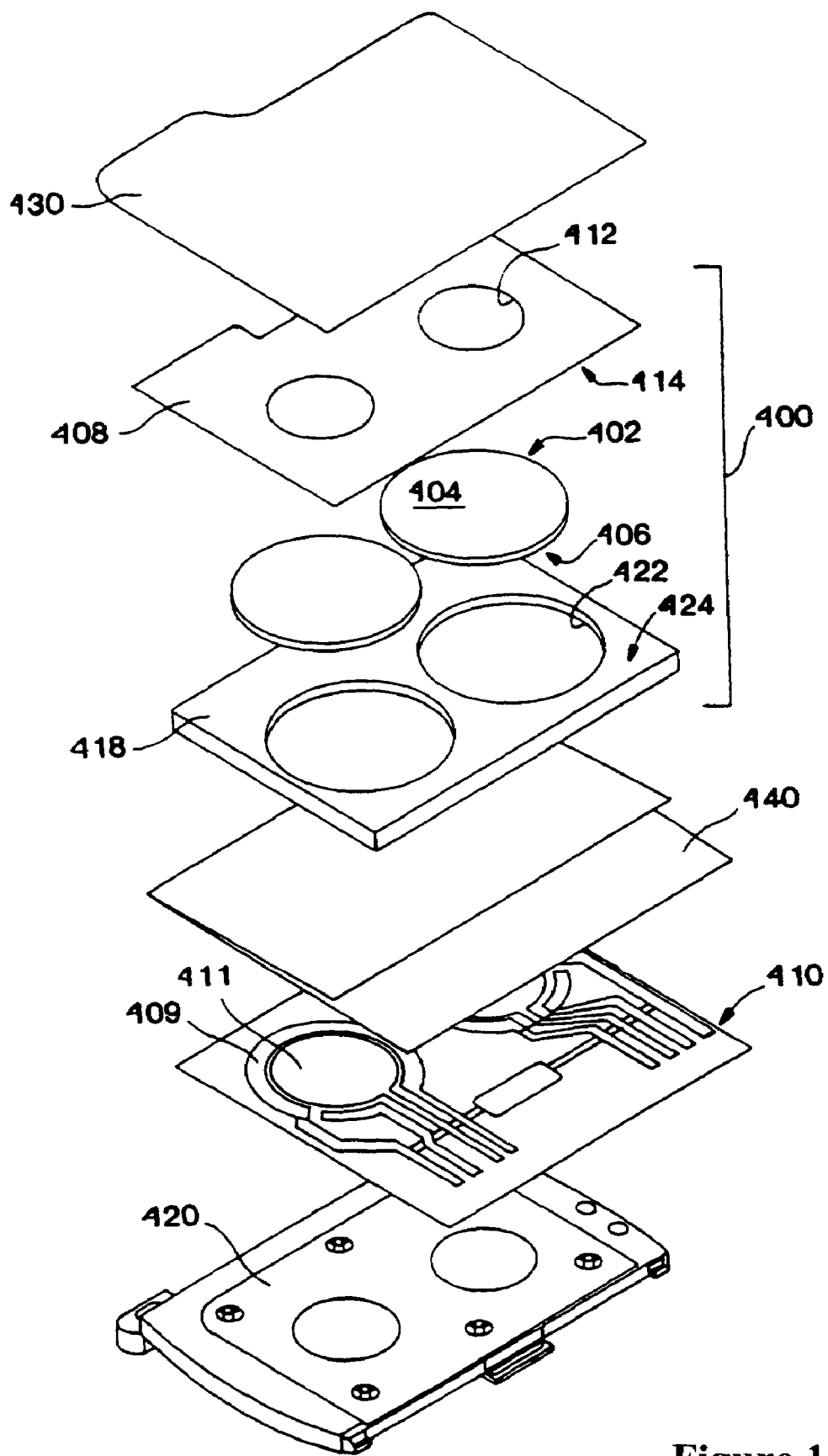
FIG. 1B presents a schematic of an exploded view of exemplary components comprising a second embodiment of an AutoSensor for use in a monitoring system. This AutoSensor exemplifies a second embodiment of a collection assembly/electrode assembly.

Referring now to FIG. 1B, a related embodiment of an exemplary collection assembly is generally indicated at 400. The assembly 400 may be aligned with an electrode assembly 410 which includes iontophoretic 409 and sensing electrodes 411 as described herein, and is adapted to be held by a tray 420 as also described herein. The collection assembly 400 includes one or more collection inserts or collection reservoirs 402 that are comprised of an ionically conductive material, and each collection reservoir defines first and second opposing surfaces, 404 and 406, respectively.

The first opposing surface 404 of the collection reservoir 402 is intended for contact with a target surface (e.g., skin or mucosal surface), and the second opposing surface 406 is intended for contact with, for example, the electrode assembly 410, thereby establishing a flow path between the target surface and the iontophoretic and sensing electrodes. As described herein, a mask layer 408 is positioned over the first surface 404 of the collection reservoir, and includes one or more openings 412 which provide for a collimated flow path between the target surface and the electrode assembly as also described herein. The opening 412 in the mask layer 408 is typically sized smaller in at least one dimension relative to the surface area of the collection reservoir 402.

A top surface 424 of a second layer 418 is positioned in facing relation with the bottom surface 414 of mask layer 408. The second layer comprises a gasket that has at least one opening 422. A two-layer laminate is formed when the mask and second layers are attached at their respective facing surfaces. The second layer also defines the collection reservoir 402 which is disposed within, and substantially fills the opening 422.

The physical and material properties of the mask layer are substantially identical to those of the mask layer described herein, and the size and shape of the one or more openings are also determined to suit the particular device. Furthermore, techniques for manufacture and manipulation of the mask layer 408 are substantially identical to those techniques described herein. However, unlike the above-described retaining layer, the gasket in the second layer 418 of the present embodiment is intended to serve as a corral for the collection reservoir. More particularly, the gasket maintains the collection reservoir in a particular orientation such that, when the collection assembly is combined (contacted) with the electrode assembly, the collection reservoir is properly aligned with the iontophoretic and sensing electrodes. The gasket material further provides for electrical and/or chemical isolation between multiple collection reservoirs, and provides structure to the collection assembly.

The second layer gasket can be formed from any suitable material such as those materials used in the mask and retaining layers of the present invention. The gasket material could be a foam material that is sized to fit within the dimensions of the tray 420. Exemplary gasket materials include, without limitation, polyethylene (PE), foamed PE, polypropylene (PP), polyethylene terephthalate (PET), polyurethane (PU), nylon, flexible polyvinylchloride (PVC), natural rubber, synthetic rubber, and suitable combinations of the foregoing materials. The gasket material can further have an adhesive coating or layer that contacts the electrode assembly and provides for the facile alignment between the electrode and collection assemblies.

Optional release liners 430 and/or 440 (a plow-fold liner) can also be respectively applied against the mask layer 408 and second layer 418 to facilitate handling of the collection assemblies as described herein. Furthermore, pre-assembled collection assembly laminates are preferably packaged, either individually or in groups.

Collection reservoirs defined by a corral or gasket can be used in devices employing a number of sampling and/or sensing devices. Typically, the collection reservoir is in operative contact with the sampling and/or sensing devices.

The components shown in exploded view in FIGS. 1A and 1B are intended for use in a automatic sampling system which is configured to be worn like an ordinary wristwatch, as described, for example, in PCT International Publication No. WO 96/00110. The wristwatch housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (for example, timing of sampling and sensing, and alternating polarity between electrodes), connectivity, computational methods, different aspects of data manipulation (for example, acquisition, recording, recalling, comparing, and reporting), etc.

The sensing electrode can be, for example, a Pt-comprising electrode configured to provide a geometric surface area of about 0.1 to 3 $cm^2$, preferably about 0.5 to 2 $cm^2$, and more preferably about 1–1.5 cm$^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof.

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per cm$^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also typically formulated using analytical- or electronic-grade reagents and solvents, and the polymer binder composition is selected to be free of electrochemically active contaminants which could diffuse to the biosensor to produce a background current.

The automatic sampling system can transdermally extract the sample over the course of a selected period of time using reverse iontophoresis. The collection reservoir comprises an ionically conductive medium, preferably a hydrogel medium having between about 125 mM to 500 mM phosphate buffer, using potassium salts of phosphate and chloride as described herein. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (for example, glucose) within a reservoir is also in contact with the reservoir. Typically, there are two collections reservoirs, each comprising glucose oxidase, and each in operative contact with iontophoretic electrode and a sensing electrode. The iontophoretic electrode may be a bimodal electrode that also serves, non-concurrently, as a counter electrode to the sensing electrode (see, for example, U.S. Pat. No. 5,954,685).

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT International Publication No. WO 96/00110. Typically, the electrical potential is alternated between two reservoirs to provide extraction of analyte into each reservoir in an alternating fashion (see, for example, U.S. Pat. Nos. 6,023,629, 5,954,685). Analyte is also typically detected in each reservoir.

As an example, to extract glucose, the applied electrical current density on the skin or tissue can be in the range of about 0.01 to about 2 mA/cm$^2$. In order to facilitate the extraction of glucose, electrical energy can be applied to the electrodes, and the polarity of the electrodes can be, for example, alternated so that each electrode is alternately a cathode or an anode. The polarity switching can be manual or automatic. Devices and methods for sampling of substances using alternating polarity are described in U.S. Pat. Nos. 6,298,254, 6,023,629, and 5,771,890.

When a bimodal electrode is used (e.g., U.S. Pat. No. 5,954,685), during the reverse iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (e.g., using a statistical technique or algorithm or combination of techniques) so that the system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,180,416, 6,326,160, 6,272,364, 6,546,269, 6,233,471, 6,144,869, 6,356,776, 6,594,514, 6,299,578, 6,309,351 and 6,595,919.

In a further aspect of the present invention, the sampling/sensing mechanism and user interface may be found on separate components (see, e.g., U.S. Pat. No. 6,561,978). Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

4.0 Exemplary Analytes and Enzymes

The analyte can be any one or more specific substance, component, or combinations thereof that one is desirous of detecting and/or measuring in a chemical, physical, enzymatic, optical analysis, or combinations thereof.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, one or more enzymes can be disposed within the one or more collection reservoirs (e.g., in the hydrogels of the present invention). The selected enzyme is capable of catalyzing a reaction with the extracted analyte to the extent that a product of this reaction can be sensed, e.g., can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase (GOx) is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytoin), chemotherapy (e.g., adriamycin), hyperactivity (e.g., ritalin), and anti-organ-rejection (e.g., cyclosporin).

Preferably, a sensor electrode is able to detect the analyte that has been extracted into the one or more collection reservoirs when present at nominal concentration levels. Suitable exemplary biosensor electrodes and associated sampling systems as described in are described in PCT International Publication Nos. WO 97/10499 and WO 98/42252.

A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl). The glucose is detected, e.g., using glucose oxidase and detecting the hydrogen peroxide reaction product.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea.

EXPERIMENTAL

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Exemplary Hydrogel Formulations

Table 1 presents the components of three exemplary hydrogel formulations.

TABLE 1

| Number | pH | PEO[1]/ (% w/w) | Bis[2]/ (% w/w) | NaH$_2$PO$_4$[3]/ (% w/w) | NaH$_2$PO$_4$[3]/ (% w/w) | NaCl[4]/ (% w/w) | H$_2$O/ (% w/w) | UA[5]/ (% w/w) | Total PO$_4^{2-}$/ (mM) | Total Cl$^-$/ (mM) |
|---|---|---|---|---|---|---|---|---|---|---|
| A | 7.4 | 10.0 | 1 | 0.26 | 2.17 | 0.9 | 84.93 | 0.2 | 100 | 150 |
| B | 7.4 | 10.0 | 1 | 0.52 | 4.34 | 0.9 | 82.54 | 0.2 | 200 | 150 |
| C | 7.4 | 10.0 | 1 | 0.78 | 6.54 | 0.9 | 80.11 | 0.2 | 300 | 150 |

[1]PEO: polyethylene oxide, Mr 600,000.
[2]Bis: bisacrylamide is % w/w of a 2% stock methylene bis acrylamide solution.
[3]In some formulations, particular where the total PO$_4^{2-}$ concentration is greater than about 200 mM, it is preferable (for some applications) to use potassium phosphate salts.
[4]The Cl$^-$ ion concentration is typically 0.9% regardless of the chloride salt used. For example, in some formulations, particular where the total PO$_4^{2-}$ concentration is greater than about 200 mM, it is preferable (for some applications) to use KCl as the Cl$^-$ ion source.
[5]UA: Undecylenic acid as sodium salt.

Nominal (Standard) Glucose oxidase enzyme (GOx) loading is typically about 2,000 units/gram of mix (approx. 0.5% w/w powder in mix). This brings the formulations in Table 1 up to a total weight percent of 100%. GOx activity assay (for units of enzyme) was based on the method of Bergmeyer, H. U. (Methods in Enzymatic Analysis, 3 rd Edition (1983), Vol II, p. 201–203).

The components were mixed at room temperature. The mixture thus obtained was coated onto sheets of a support substrate (e.g., Delnet or Reemay fabric). Typically Delnet non-woven fabric was used. Cross-linking was carried out by exposure to about 0.3 to 0.6 Mrad ebeam irradiation at room temperature. Essentially circular hydrogels of about 0.75 inch and 0.007 inch thickness were punched out of the sheets. The hydrogels thus obtained were used for the flux and mutarotation studies, and their performance was measured as described below.

In some embodiments it is advantageous to use potassium as the counter-ion due to its increased solubility characteristics as opposed to sodium. For example, at room temperature, both sodium phosphate and potassium phosphate are soluble in water. However, as the temperature is lowered (e.g., refrigeration at 5° C.), potassium phosphate remains soluble whereas sodium phosphate falls out of solution. In some cases, compositions of the present invention, for example, buffer systems or hydrogels, may be refrigerated or exposed to cold temperatures in transit. Accordingly, in such situations it is practical to increase the phosphate concentration using potassium as the counter-ion. In such cases the Cl⁻ counterion is also typically potassium.

For some applications, mixtures of potassium and sodium salts may be employed (e.g., mixtures of KCl and NaCl, and/or mixtures of potassium and sodium phosphate salts).

Example 2

Analyte Flux

A. Buffer Systems

Analyte flux was measured across skin surface using the exemplary analyte glucose. Glucose flux across skin surface was determined as a function of buffer composition. Buffer systems had varying concentrations of phosphate buffer (formulated from sodium salts of monobasic and dibasic phosphate) and pH. The electrolyte concentration was the same for all buffers (0.9% NaCl). In general, two Ag/AgCl electrode, liquid reservoir systems (i.e., two collection reservoir chambers) were placed on each arm of a subject. The current was provided using Iomed Phoresors (Iomed, Salt Lake City, Utah) using an alternating polarity scheme. Briefly, the current was applied for 7.5 minutes for current flow in a first direction, then the polarity was switched so current flowed in the reverse direction, i.e., a second direction, for 7.5 minutes. Thus, each reservoir received the same amount of anodal and cathodal iontophoresis in the 15 period. Current was 0.7 mA=0.25 mA/cm².

The extraction period (iontophoresis period) was 15 min., followed by a 5 min. period where the current was turned off allowing for the buffer to be extracted, fresh buffer to be added, and fingerpricks to be performed as necessary. The first 60 minutes of each study was used to equilibrate the arm. In addition, the first extraction period after the concentration of the buffer was changed was used for equilibration, therefore, data was not included in the calculation of flux. The average flux values of glucose extracted from three subjects two systems per subject, two reservoirs per system (12 skin sites) are given in Table 2 below.

TABLE 2

| pH | Phosphate Concentration (mM) | Average Flux (nmol/cm²-hr) |
|---|---|---|
| 6.0 | 250 | 0.69 |
| 6.0 | 350 | 0.63 |
| 6.5 | 125 | 1.15 |
| 6.5 | 250 | 1.25 |
| 7.5 | 50 | 2.09 |
| 7.5 | 100 | 2.52 |
| 7.5 | 200 | 2.74 |

Average Glucose Flux at Different Phosphate Concentrations.

Thus, flux of glucose into the buffer can be increased by increasing the pH of the buffer (e.g., compare pH 6.0, 250 mM phosphate to pH 6.5 250 mM phosphate), and/or by increasing the total concentration of the buffer (e.g., compare pH 6.5, 125 to 250 mM phosphate concentration, and pH 7.5, 50–200 mM phosphate concentration).

B. Data from AutoSensors Using Hydrogels Having Different Phosphate Buffer Concentrations.

Six human subjects were used. Each subject wore eight GlucoWatch biographers (four per condition). Two conditions were tested:

Condition 1: Control (100 mM sodium phosphate hydrogels)
Condition 2: 200 mM potassium phosphate hydrogels Hydrogels were made essentially as described in Example 1 except potassium monobasic and dibasic phosphate were used (when indicated) instead of sodium monobasic and dibasic phosphate. The study duration was 14 hours 58 minutes. Reference blood glucose measurements were taken at least two times per hour. The reference blood measurements were taken twenty minutes prior to the corresponding GlucoWatch biographer measurements to account for the twenty minute lag time between taking the reference blood glucose measurement (i.e., by fingerstick) and obtaining the corresponding glucose measurement using the GlucoWatch biographer.

Average baseline values were temperature corrected with respect to desired calibration time and calculated using previous baseline-determined calculations. Graphs of integrated GlucoWatch biographer signals (in units of nC) were made for sensors A and B on the primary y-axis and reference blood glucose (in units of mg/dl) on the x-axis. Data for the 2–9 hour period were processed using ordinary least squares linear regression to obtain $R^2$, slope and intercept.

The results of this experiment compared phosphate concentration and/or its counter ion—sodium versus potassium—on the performance of analyte monitoring systems. Two conditions were evaluated: 1) Control (100 mM sodium phosphate gels) and 2) 200 mM potassium phosphate gels. Table 3 summarizes the results.

TABLE 3

| Condition | $R^2$ Sensor A + B | Least Squares Slope (nC/(mg/dL)) Sensor A + B | Least Squares Intercept (nC) Sensor A + B |
|---|---|---|---|
| Control (100 mM sodium phosphate hydrogels) | 0.41 | 207 | −3079 |
| 200 mM potassium phosphate hydrogels | 0.31 | 299 | −1587 |

Analyte sensitivity, which is the slope of the regression line (amount of charge signal divided by the concentration of glucose in blood), using the 200 mM sodium phosphate gel condition was much greater (44%) than for the control condition. The difference between means was statistically significant. Overall, slopes were much higher for the 200 mM potassium phosphate condition than for the control. Results of these experiments support the conclusion that increasing the gel's phosphate buffer concentration increases transdermal glucose flux.

C. Data from AutoSensors Using Hydrogels Having Different Phosphate Buffer Concentrations and Two Different Structural Supports.

The results presented above explored the effects of increased phosphate concentration in the gel. The two conditions investigated included 100 mM sodium phosphate gels and 200 mM potassium phosphate gels (Delnet scrim for both conditions).

Six human subjects were used in this experiment. Each subject wore eight GlucoWatch biographers (two per condition). Four conditions tested were as follows:

Condition 1: Control (100 mM sodium phosphate gel with Delnet)

Condition 2: 200 mM potassium phosphate gel (Delnet)
Condition 3: 200 mM potassium phosphate gel (Reemay)
Condition 4: 300 mM potassium phosphate gel (Delnet)

The study duration was 14 hours 58 minutes. Reference blood glucose measurements were taken at least two times per hour. The reference blood measurements were taken twenty minutes prior to the corresponding GlucoWatch biographer measurements to account for the twenty minute lag time between taking the reference blood glucose measurement (i.e., by fingerstick) and obtaining the corresponding glucose measurement using the GlucoWatch biographer.

Average baseline values were temperature corrected with respect to desired calibration time and calculated using previous baseline-determined calculations. Graphs of integrated GlucoWatch biographer signals (in units of nC) were made for sensors A and B on the primary y-axis and reference blood glucose (in units of mg/dl) on the x-axis. Data were processed using ordinary least squares linear regression to obtain $R^2$, slope and intercept.

The effect of gel phosphate concentration on increased analyte flux and sensitivity was evaluated as described. The gel formulations were essentially as described in Example 1, with the exception that potassium salts were used for phosphate buffers and electrolytes when indicated. Table 4 summarizes the unscreened results of these experiments.

TABLE 4

| Condition | $R^2$ Sensor A + B | Least Squares Slope (nC/(mg/dL)) Sensor A + B | Least Squares Intercept (nC) Sensor A + B |
|---|---|---|---|
| Control (100 mM sodium phosphate gel with Delnet) | 0.69 | 175 | −6049 |
| 200 mM potassium phosphate gel (Delnet) | 0.61 | 258 | −5009 |
| 200 mM potassium phosphate gel (Reemay) | 0.58 | 280 | −4263 |
| 300 mM potassium phosphate gel (Delnet) | 0.56 | 274 | 294 |

Sensitivity was approximately 47% higher for the 200 mM Delnet condition than for the control. This percentage increased to 60% and 56% for the 200 mM Reemay and 300 mM Delnet conditions, respectively, compared with the control. Before application of any signal screens, the highest slope was observed for the 200 mM phosphate with Reemay condition. For the 300 mM phosphate with Delnet and 200 mM phosphate with Delnet conditions slightly lower slopes were observed. Results of these experiments support the conclusion that increasing the gel's phosphate buffer concentration above 100 mM improves performance.

D. Data from AutoSensors Using Hydrogels Having Different Phosphate Buffer Concentrations and Two Different Ink Formulations.

Eight human subjects were used. Each subject wore eight GlucoWatch biographers (two per condition). Four conditions were tested:

Condition 1: Control (Standard Sensor ink, Standard Hydrogel—100 mM sodium phosphate and Delnet scrim).
Condition 2: Standard Sensor ink, High Phosphate Hydrogel—200 mM potassium phosphate with Reemay scrim
Condition 3: Alternative Sensor ink, Standard Hydrogel—100 mM sodium phosphate and Delnet scrim.
Condition 4: Alternative Sensor ink, High Phosphate Hydrogel—200 mM potassium phosphate with Reemay scrim The alternative ink formulation has been described in PCT International Publication No. WO 03/054070. Briefly, the formulation of the alternative ink sensor was as follows: Pt/C ink (1% Pt), consists of a mixture of Poly(styrene-co-methyl methacrylate) polymer binder, Ethylene glycol diacetate solvent, graphite, and Pt/C. Briefly, a medium was prepared by mixing one part poly (styrene-co-methyl methacrylate) (Aldrich, catalog #46,289-6) and three parts ethylene glycol diacetate (EGDA). Approximately 22.42 g of the polystyrene-co-methyl-methacrylate was dissolved in about 46.19 g EGDA. To the medium were added 20.63 g graphite (Timrex SFG-15, Timcal), and 5.5 g 5% platinum-on-graphite (Type 98199, Johnson-Matthey). The solution was mixed by hand until a homogenous mixture was obtained. This results in an ink formulation having 1% platinum catalyst. The ink was then subjected to high shear mixing with a triple-roll mill. Three passes through the mill were typically used. The jar of ink was kept rolling on a jar roller to maintain dispersion of the ingredients and to prevent settling. Before printing, additional EGDA may be added to adjust the viscosity for optimal printing. Ink screen-printing was performed using a 180 mesh stainless steel screen and a 90 durometer squeegee.

The standard ink sensor has been previously described (see, e.g., EP 0 942 278, GB 2 335 278, U.S. Pat. No. 6,587,705).

The study duration was 14 hours, 58 minutes. Reference blood glucose measurements were taken at least two times per hour. The reference blood measurements were taken twenty minutes prior to the corresponding GlucoWatch biographer measurements to account for the twenty minute lag time between taking the reference blood glucose measurement (i.e., by fingerstick) and obtaining the corresponding glucose measurement using the GlucoWatch biographer.

Average baseline values were temperature corrected with respect to desired calibration time and calculated using previous baseline-determined calculations. Graphs of integrated GlucoWatch biographer signals (in units of nC) were made for sensors A and B on the primary y-axis and reference blood glucose (in units of mg/dl) on the x-axis. Data were processed using ordinary least squares linear regression to obtain $R^2$, slope and intercept.

The results of this experiment compared the performance of analyte monitoring systems employing high phosphate hydrogels and sensors printed with an alternative ink formulation. The four phosphate concentration/ink formulation combinations examined were: 1) Control (standard ink/100 mM sodium phosphate hydrogel with Delnet), 2) Standard ink/200 mM potassium phosphate hydrogel with Reemay, 3) Alternative ink formulation/100 mM sodium phosphate hydrogel with Delnet, and 4) Alternative ink formulation/ 200 mM potassium phosphate hydrogel with Reemay. The following Table 5 summarizes the results.

TABLE 5

| Condition | $R^2$ Sensor A + B | Least Squares Slope (nC/(mg/dL)) Sensor A + B | Least Squares Intercept (nC) Sensor A + B |
|---|---|---|---|
| Control (Standard Sensor, Standard Hydrogel - 100 mM | 0.63 | 113 | −187 |

TABLE 5-continued

| Condition | $R^2$ Sensor A + B | Least Squares Slope (nC/(mg/dL)) Sensor A + B | Least Squares Intercept (nC) Sensor A + B |
|---|---|---|---|
| sodium phosphate and Delnet scrim) | | | |
| Standard Sensor, High Phosphate Hydrogel - 200 mM potassium phosphate with Reemay scrim | 0.51 | 169 | 3635 |
| Alternative ink, Standard Hydrogel - 100 mM sodium phosphate and Delnet scrim. | 0.50 | 146 | 4057 |
| Alternative ink, High Phosphate Hydrogel - 200 mM potassium phosphate with Reemay scrim | 0.45 | 184 | 8771 |

Sensitivity was the highest for the two high phosphate hydrogel conditions; but the alternative ink/standard hydrogel condition also displayed greater sensitivity than the control. Sensitivity was the highest for the alternative ink/high phosphate hydrogel condition, suggesting that the high phosphate hydrogel and the alternative ink each positively influences performance.

Increasing the phosphate concentration in the hydrogel also reduced the percent of skipped signals due to the A/B screen of the GlucoWatch biographer. This screen is a data integrity screen used in the GlucoWatch biographer. The GlucoWatch biographer has two sensing electrodes (sensor A and sensor B). In a typically measurement cycle, iontophoretic extraction is carried out into a first hydrogel in contact with sensor A and then into a second hydrogel in contact with sensor B. The A/B screen compares the analyte-related signal (in this case, the glucose-related signal) obtained in a first hydrogel relative to second hydrogel. If there is a significant discrepancy between the two values, based on a predetermined acceptable error, then the two values are not used to calculate a glucose value and the glucose measurement from that cycle is a "skip."

These results demonstrate improved sensitivity of an analyte monitoring device when the device employs hydrogels having a higher phosphate buffer concentration than 100 mM phosphate buffer.

The enhanced signal, observed in the above-described experiments, related to increased phosphate concentration could either be due to a larger glucose concentration available for detection in the hydrogel or buffer system (i.e., higher skin flux of glucose) or due to greater detection of glucose (i.e., greater mutarotation rate).

Three variables (pH, phosphate concentration, and temperature) affect the rate of mutarotation of glucose, and temperature additionally affects the rate of diffusion of glucose into the hydrogel. Higher current values over a set period of time are expected when the rate of mutarotation is increased.

Hydrogels used in the study described in Table 5 were used in a bench experiment to evaluate signal recovery. Each sensor was spiked with known amounts of glucose in solution. The current was measured following the spike and integrated to get the charge produced by the glucose spike.

The recovery of the glucose spike was determined by:

% recovery=(experimental charge/theoretical charge) 100 where the theoretical charge was calculated from mass balance and corresponds to 386,000 nA*S (nA (times) seconds) for the amount of glucose used in the experiments, and the experimental charge was obtained by integrating the area under the curve for the current measured. The percent recovery was calculated at seven minutes. Seven minutes was the duration of biosensor activation per sensing period in the human studies described in Examples 2B–2D. The data is given in Table 6.

TABLE 6

| Hydrogel/Sensor | Percent Recovery 7 minutes |
|---|---|
| Control (100 mM Phosphate Buffer)/Standard Ink Sensor | 72% |
| 200 mM Phosphate/ Standard Ink Sensor | 80% |
| Control (100 mM Phosphate Buffer)/Alternative ink Sensor | 68% |
| 200 mM Phosphate/ Alternative ink Sensor | 79% |

An increase in the observed percent recovery is likely related to the increased rate at which mutarotation of glucose occurs. Thus, mutarotation of glucose was seen to increase in the hydrogel compositions of the present invention as evidenced by higher percent recovery of glucose in hydrogels having higher phosphate buffer concentrations. However, this increase in signal is not as large as the total increase in signal as observed in Tables 3, 4, and 5. Thus, the increased signal can be attributed primarily to enhanced glucose flux when using the hydrogels of the present invention. This result is consistent with the results of Example 2 that demonstrated higher skin flux of analyte using the higher phosphate concentration buffers of the present invention.

Example 3

Clinical Studies and Results Concerning Performance of the High Phosphate Gels of the Present Invention The high phosphate hydrogels of the present invention were used in clinical trials to confirm the efficacy and benefits of the high phosphate hydrogels of the present invention. The tested conditions included the following:

Condition 1: Control (Standard Sensor ink, Standard Hydrogel—100 mM sodium phosphate and Delnet scrim.

Condition 2: Alternative Sensor ink, Standard Hydrogel—100 mM sodium phosphate and Delnet scrim.

Condition 3: Standard Sensor ink, High Phosphate Hydrogel—200 mM potassium phosphate with Delnet scrim.

Condition 4: Alternative Sensor ink, High Phosphate Hydrogel—200 mM potassium phosphate with Delnet scrim.

The clinical trial population consisted of 66 subjects: age 18 years and older (Mean age=45.1); and, 41 females and 25 males with type 1 or type 2 diabetes mellitus (55 Type 1, 11 Type 2). GlucoWatch G2 biographers, providing each of the above-described four conditions, were applied to each subject on forearm sites and run for 15 hours. Fingerpricks were taken every 30 minutes starting at elapsed time (ET) 0:55. GlucoWatch G2 biographers were worn in a home environment. Reference blood measurements were taken 20 minutes prior to the corresponding biographer measurement to account for 20 minutes of lag time. Reference blood measurements were taken using a One Touch® Ultra (Johnson & Johnson, New Brunswick, N.J.) blood glucose meter.

The GlucoWatch G2 biographers were research versions of the device that were used to collect all of the raw data typically collected by a GlucoWatch G2 biographer; but the device performed no calculations based on the raw data, for example, the device did not calculate a glucose measurement value. Accordingly, glucose readings were not provided to the users. The raw data from the research GlucoWatch G2 biographers was stored to a data file called MLOG. Exemplary data saved to the MLOG file included, but was not limited to, elapsed time, temperature data, first sensor current readings (in nA), second sensor current readings. Further information concerning MLOG can be found, for example, in United States Patent Application Publication No. 20020045808. The MLOG data allowed for various analyses to be performed. Statistical analyses were performed using SAS® for Windows (Version 8) (SAS Institute Inc., Cary, N.C.) and/or Visual Basic for Applications (Microsoft Corporation, Redmond, Wash.).

These analyses differ from those generally performed on clinical data in that they focused primarily on GlucoWatch G2 biographer nA signal. Emulator programs, employing baseline subtraction and integration (see, e.g., U.S. Pat. No. 6,233,471), were used to calculate nC results based on the nA signals. As part of the standard analysis, the 2-hour point was used as the $1^{st}$ point to produce nC regression tables. Average background values were temperature corrected with respect to the expected value at calibration (CAL time; ET 2:15) and calculated using previous baseline subtraction. Analysis of Variance (ANOVA) was performed for correlation coefficients. Least squares nC slope and intercept values for ET2:00–15:00 were calculated.

The coefficient of determination ($R^2$), least squares slope (nC/mg/dL), and least squares intercept (nC) are presented for unscreened nC data, for ET 2:00–9:00, in Table 7. The nC readings were based on readings from both sensors of the GlucoWatch G2 biographer for a given measurement cycle (i.e., sensor A+sensor B).

From the data presented in Table 7 several important conclusions may be drawn. The most relevant pair-wise comparisons for the data in Table 7 are between conditions 1 and 3, and 2 and 4. These pair-wise conditions are made between sensors fabricated from the same ink compositions, thus having the same electrochemical properties. Comparison of $R^2$ results showed consistent results for all conditions. Comparison of the least squares slopes showed a statistically significant difference ($p<0.0001$) for comparison of both conditions 1 and 3, and 2 and 4. The higher least squares slopes seen in conditions 3 and 4 indicated a greater sensitivity for those two conditions, which can be attributed to the high phosphate hydrogels used in both of these conditions.

These results demonstrate a significant advantage of using the high phosphate gels of the present invention for the detection of analyte, in that use of the high phosphate gels resulted in higher analyte sensitivity when using the high phosphate gels with sensing electrodes for electrochemical detection of analyte.

CalRatio values for the different conditions were also evaluated. The CalRatio check provides a screen for valid or efficacious calibration readings (see, e.g., U.S. Pat. No. 6,326,160). The screen is employed in analyte monitoring devices, for example, the GlucoWatch G2 biographer. It has been previously determined that if the CalRatio falls outside of a preselected range of values, then the calibration should be rejected and the calibration re-done. CalRatio is defined as follows:

$$\text{CalRatio} = (BG/cp)/(\text{active}/cp + \text{offset})$$

In the CalRatio, "BG/cp" was the blood glucose concentration at the calibration point (or calibration time), "active/cp" was, in this case, the integrated biosensor signal (nC) at the calibration point, and "offset" was a constant offset, where the offset takes into account the intercept value. The offset value was established empirically using standard error minimization routines to evaluate a number of potential offset values for a large data set, and thereby select the one that results in the most accurate prediction of blood glucose. For the GlucoWatch G2 biographer, the acceptable CalRatio range was established using standard error minimization routines to evaluate a large population of calibration points, and thereby determine the CalRatio values that result in accurate blood glucose predictions.

The results of the CalRatio analysis are presented in Table 8.

TABLE 7

| Condition | | $R^2$ | Least Squares Slope | Least Squares Intercept |
|---|---|---|---|---|
| 1: Control: Standard Sensor ink, Standard Hydrogel | Average Standard Deviation | 0.63 0.31 | 142 116 | −3072 20275 |
| 2: Alternative Sensor ink, Standard Hydrogel | Average Standard Deviation | 0.55 0.29 | 162 131 | −1753 12407 |
| 3: Standard Sensor ink, High Phosphate Hydrogel | Average Standard Deviation | 0.61 0.30 | 253 173 | −6615 24906 |
| 4: Alternative Sensor ink, High Phosphate Hydrogel | Average Standard Deviation | 0.57 0.30 | 253 181 | −7988 26346 |

TABLE 8

| Condition | | CalRatio |
|---|---|---|
| 1: Control: Standard Sensor ink, Standard Hydrogel | Average Standard Deviation | 0.0087 0.0055 |
| 2: Alternative Sensor ink, Standard Hydrogel | Average Standard Deviation | 0.0063 0.0035 |
| 3: Standard Sensor ink, High Phosphate Hydrogel | Average Standard Deviation | 0.0039 0.0016 |
| 4: Alternative Sensor ink, High Phosphate Hydrogel | Average Standard Deviation | 0.0038 0.0016 |

The Control condition had the highest CAL Ratio value, 0.0087, of the four conditions (i.e., it was the least sensitive condition). Condition 2 (Alternative Sensor ink, Standard Hydrogel) had a lower CalRatio value, 0.0063. Conditions 3 (Standard Sensor ink, High Phosphate Hydrogel) and 4 (Alternative Sensor ink, High Phosphate Hydrogel) showed much lower CalRatio values (0.0039; 0.0038, respectively) showing overall improved sensitivity attributable to the high phosphate hydrogel. In the GlucoWatch G2 biographer, the CalRatio threshold is 0.015 (i.e., at CalRatio values above 0.015 the calibration is rejected and the calibration re-done). Further, the distribution (not shown) of all CalRatio values in the study was more concentrated around lower values in Condition 2 and even more so in conditions 3 and 4.

The study data demonstrated that the high phosphate gels of the present invention performed better than the Control condition.

Example 4

Clinical Studies and Results Concerning Failed Calibration Attempts and Recalibration Performance The analysis in this example is based on data obtained in the clinical study described above in Example 3. In this study, 60 GlucoWatch G2 biographers with the standard hydrogel (Condition 1) and 58 GlucoWatch G2 biographers with the high phosphate hydrogel (Condition 3) had at least one attempted calibration. Out of 60 GlucoWatch G2 biographers with the standard hydrogel, 52 (87%) calibrated successfully. Out of 58 GlucoWatch G2 biographers with the high phosphate hydrogel with attempted calibrations, 58 (100%) calibrated successfully. Table 9 summarizes the frequency of failed calibration attempts per GlucoWatch G2 biographer use. A greater number of GlucoWatch G2 biographers with the high phosphate hydrogel calibrated successfully on the first try: 75%–77% of GlucoWatch G2 biographers with the standard hydrogel vs. 95%–97% of GlucoWatch G2 biographers with the high phosphate hydrogel. The difference in the percentage of GlucoWatch G2 biographers that calibrated successfully on the first try was statistically significant (p-value=0.002). Table 9 presents the data related to frequency of failed calibration attempts excluding recalibrations by GlucoWatch G2 biographer use.

TABLE 9

| # (%) of Failed Calibrations Per GlucoWatch G2 biographer Use | Condition 1 | Condition 3 |
| --- | --- | --- |
| 0 | 46 (77%) | 56 (97%) |
| 1 | 4 (7%) | 1 (2%) |
| 2 | 1 (2%) | 1 (2%) |

TABLE 9-continued

| # (%) of Failed Calibrations Per GlucoWatch G2 biographer Use | Condition 1 | Condition 3 |
| --- | --- | --- |
| 3 | 1 (2%) | 0 |
| 4 | 8 (13%) | 0 |
| Total | 60 (100%) | 58 (100%) |

Out of all GlucoWatch G2 biographers with the standard hydrogels that had a calibration attempt (60 GlucoWatch G2 biographers), 14 GlucoWatch G2 biographers had at least one failed attempt to calibrate. Out of all GlucoWatch G2 biographers with the high phosphate hydrogels that had a calibration attempt (58 GlucoWatch G2 biographers), 2 GlucoWatch G2 biographers had at least one failed attempt to calibrate. Eight GlucoWatch G2 biographers with the standard hydrogels had a maximum possible number of failed calibration attempts (four) and shut off. None of the GlucoWatch G2 biographers with the high phosphate hydrogel shut off due to failed calibration attempts.

Table 10 summarizes the calibration attempts. Out of a total of 61 calibration attempts for the GlucoWatch G2 biographers with the high phosphate hydrogel, 58 (95%) resulted in a successful calibration. For the standard hydrogel, only 56% of calibration attempts were successful. Table 10 presents a summary of calibration attempts excluding recalibrations.

TABLE 10

| Category | Condition 1 | Condition 3 |
| --- | --- | --- |
| # of Successful Calibrations | 52 (56%) | 58 (95%) |
| # of Failed Calibration | 41 (44%) | 3 (5%) |
| # of All Calibration | 93 (100%) | 61 (100%) |

Most of the failed calibration attempts for GlucoWatch G2 biographer with the standard hydrogel were due to data integrity checks implemented to ensure that the sensitivity of the system is sufficient to adequately measure glucose (Table 11). The sizable reduction in percentage of failed calibration attempts (from 44% for the standard hydrogel to 5% for the high phosphate hydrogel, i.e. ~8 fold) was likely due to the larger signal produced by the high phosphate hydrogel. Table 11 presents data relating to the reasons for failed calibration attempts (excluding recalibrations) for GlucoWatch G2 biographers. In Table 11, PRSP is a failure related to perspiration, TEMP is a failure related to temperature fluctuation, COLD is a failure related to temperature below a predetermined threshold, DATA is a failure related to a data integrity check (including a CalRatio check), VOLT is a failure related to ionotophoretic voltage fluctuation.

TABLE 11

| Reasons for Failed Calibration attempts | Condition 1 | | | Condition 3 | | |
| --- | --- | --- | --- | --- | --- | --- |
| | # of Failed CAL | % of Total Failed CAL Attempts | % of Total CAL Attempts | # of Failed CAL | % of Total Failed CAL Attempts | % of Total CAL Attempts |
| PRSP | 2 | 5% | 2% | 0 | 0% | 0% |
| TEMP | 0 | 0% | 0% | 0 | 0% | 0% |
| COLD | 0 | 0% | 0% | 0 | 0% | 0% |

TABLE 11-continued

| Reasons for Failed Calibration attempts | Condition 1 | | | Condition 3 | | |
|---|---|---|---|---|---|---|
| | # of Failed CAL | % of Total Failed CAL Attempts | % of Total CAL Attempts | # of Failed CAL | % of Total Failed CAL Attempts | % of Total CAL Attempts |
| DATA | 39 | 95% | 42% | 3 | 100% | 5% |
| VOLT | 0 | 0% | 0% | 0 | 0% | 0% |
| Total | 41 | 100% | 44% | 3 | 100% | 5% |

For GlucoWatch G2 biographers with the standard hydrogels, 7 of the GlucoWatch G2 biographers (13% of those with successful calibrations) had recalibration attempts due to consecutive skips. Out of the seven GlucoWatch G2 biographers with recalibrations, five were able to recalibrate successfully on the first try and two had one unsuccessful recalibration attempt. That led to nine recalibration attempts, of which seven were successful. For GlucoWatch G2 biographers with the high phosphate hydrogel, 4 GlucoWatch G2 biographers (7%) had recalibration attempts. All of these recalibrated successfully on the first try. Table 12 presents a summary of recalibration attempts.

TABLE 12

| Category | Condition 1 | Condition 3 |
|---|---|---|
| # of Successful | 7 | 4 |
| # of Failed Recalibration | 2 | 0 |
| # of All Recalibration | 9 | 4 |

The data presented in this example demonstrate that use of the high phosphate hydrogels, described herein, reduced the frequency of failed calibration of the GlucoWatch G2 biographer. Further, use of the high phosphate hydrogels improved recalibration attempts relative to use of a standard hydrogel (100 mM phosphate buffer).

As is apparent to one of skill in the art, various modification and variations of the above embodiments can be made without departing from the spirit and scope of this invention. Such modifications and variations are within the scope of this invention.

What is claimed is:

1. A hydrogel composition for measuring glucose flux, said hydrogel composition comprising:
a hydrophilic compound which forms a gel in the presence of water, an electrolyte, a phosphate buffer present at a concentration of between about 125 mM and about 500 mM, and a pH of between about pH 6.5 to about pH 8.5, wherein the glucose flux into the hydrogel is at least 0.65 nmol/cm$^2$hr.

2. The hydrogel of claim 1, wherein the hydrophilic compound is selected from the group consisting of polyethylene oxide, polyvinyl alcohol, polyacrylic acid, and polyvinyl pyrrolidone, and co-polymers thereof.

3. The hydrogel composition of claim 1, wherein said hydrophilic compound comprises polyethylene oxide.

4. The hydrogel composition of claim 1, wherein said hydrophilic compound is a polymer, and said polymer is present at a weight percent of between about 0.5% to about 40%.

5. The hydrogel composition of claim 1, wherein said pH is between about pH 7 to about pH 8.

6. The hydrogel composition of claim 1, wherein the hydrogel further comprises a cross-linking agent.

7. The hydrogel composition of claim 6, wherein said cross-linking agent is present at a weight percent of from about 0.001% to about 2%.

8. The hydrogel composition of claim 7, wherein said cross-linking agent is N,N'-methylenebisacrylamide.

9. The hydrogel composition of claim 1, wherein said hydrogel is treated with Electron-beam radiation to promote cross-linking within the hydrogel.

10. The hydrogel composition of claim 1, wherein said phosphate buffer comprises monobasic and dibasic phosphate.

11. The hydrogel composition of claim 10, wherein said monobasic and dibasic phosphate comprise counter ions and said counter ions are selected from the group consisting of sodium counter ions, potassium counter ions, and mixtures thereof.

12. The hydrogel composition of claim 11, wherein for said monobasic and dibasic phosphate the counter ion is potassium.

13. The hydrogel composition of claim 1, wherein said electrolyte is a chloride salt.

14. The hydrogel composition of claim 13, wherein said chloride salt is present at a weight percent of between about 0.25% to about 2%.

15. The hydrogel composition of claim 13, wherein said chloride salt is selected from the group consisting of sodium chloride, potassium chloride, and mixtures thereof.

16. The hydrogel composition of claim 15, wherein said chloride salt is potassium chloride.

17. The hydrogel composition of claim 1, wherein said hydrogel further comprises an enzyme.

18. The hydrogel composition of claim 17, wherein said analyte is glucose and said enzyme comprises glucose oxidase.

19. The hydrogel composition of claim 1, wherein the hydrogel further comprises a biocide.

20. The hydrogel composition of claim 19, wherein said biocide is selected from the group consisting of chlorinated hydrocarbons, organometallics, metallic salts, organic sulfur compounds, phenolic compounds, quaternary ammonium compounds, surfactants, membrane-disrupting agents, and combinations thereof.

21. The hydrogel composition of claim 19, wherein said biocide is undecylenic acid or a salt thereof.

* * * * *

UNITED STATES PATENT AND TRADEMARK OFFICE
CERTIFICATE OF CORRECTION

| | | |
|---|---|---|
| PATENT NO. | : 7,150,975 B2 | Page 1 of 1 |
| APPLICATION NO. | : 10/643631 | |
| DATED | : December 19, 2006 | |
| INVENTOR(S) | : Janet A. Tamada, Michael J. Tierney and Stephen C. Williams | |

It is certified that error appears in the above-identified patent and that said Letters Patent is hereby corrected as shown below:

On the Title Page, FIELD [56], References Cited, U.S. PATENT DOCUMENTS:

DELETE:

5,428,217 A   6/1995   Nakajima et al.

5,442,858 A   8/1995   Wolters et al.

5,965,879 A   10/1999   Leviton

Signed and Sealed this

Third Day of April, 2007

JON W. DUDAS
*Director of the United States Patent and Trademark Office*